(12) United States Patent
Nelson

(10) Patent No.: US 8,480,626 B2
(45) Date of Patent: Jul. 9, 2013

(54) INFUSION CATHETER ASSEMBLY WITH REDUCED BACKFLOW

(75) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 188 days.

(21) Appl. No.: 12/276,794

(22) Filed: Nov. 24, 2008

(65) Prior Publication Data
US 2009/0143764 A1 Jun. 4, 2009

Related U.S. Application Data

(60) Provisional application No. 61/005,047, filed on Nov. 30, 2007.

(51) Int. Cl.
*A61M 5/178* (2006.01)
(52) U.S. Cl.
USPC ............ 604/164.01; 604/164.08; 604/170.01; 604/164.11; 604/165.03; 604/272
(58) Field of Classification Search
USPC ................. 604/164.01, 164.08, 170.01, 6.05, 604/165.03, 272, 164.11, 264, 158–159, 604/164.07, 187
See application file for complete search history.

(56) References Cited

U.S. PATENT DOCUMENTS

| | | |
|---|---|---|
| 3,766,915 A | 10/1973 | Rychlik |
| 4,306,566 A | 12/1981 | Sinko |
| 4,350,159 A | 9/1982 | Gouda |
| 4,368,730 A * | 1/1983 | Sharrock .................. 604/158 |
| 4,917,670 A | 4/1990 | Hurley et al. |
| 5,078,702 A | 1/1992 | Pomeranz |
| 5,092,848 A | 3/1992 | deCiutiis |
| 5,092,850 A | 3/1992 | Buma |
| 5,104,705 A | 4/1992 | Quackenbush |
| 5,231,996 A | 8/1993 | Bardy et al. |
| 5,254,107 A | 10/1993 | Soltesz |

(Continued)

FOREIGN PATENT DOCUMENTS

| | | |
|---|---|---|
| DE | 39 00 635 A1 | 7/1990 |
| EP | 0 086 338 A1 | 8/1983 |

(Continued)

OTHER PUBLICATIONS

Morrison et al. Focal delivery during direct infusion to brain: role of flow rate, catheter diameter and tissue mechanics. Oct. 1999; Am. J. Physiol. pp. R1218-R1229.*

(Continued)

*Primary Examiner* — Kevin C Sirmons
*Assistant Examiner* — Edelmira Bosques
(74) *Attorney, Agent, or Firm* — Mueting, Raasch & Gebhardt, P.A.

(57) ABSTRACT

Catheters assemblies having structural configurations operable to reduce backflow along the catheter assembly track, and methods of making and using such catheter assemblies. Catheters assemblies in accordance with embodiments of the present invention find use in various applications including the treatment of acute and chronic medical conditions. An exemplary catheter assembly includes, in one illustrative embodiment, a flexible proximal catheter body portion, and a distal portion of a smaller diameter than the body portion. The distal portion includes a sealed distal tip or end and one or more side flow openings to permit flow of therapeutic substance from the catheter along an axis that is different than, e.g., skewed relative to, a longitudinal axis of the distal portion of the catheter assembly.

12 Claims, 14 Drawing Sheets

U.S. PATENT DOCUMENTS

| | | | |
|---|---|---|---|
| 5,314,463 | A | 5/1994 | Camps et al. |
| 5,403,311 | A | 4/1995 | Abele et al. |
| 5,454,491 | A | 10/1995 | Liu |
| 5,466,218 | A | 11/1995 | Srisathapat et al. |
| 5,478,328 | A * | 12/1995 | Silverman et al. ............ 604/272 |
| 5,527,307 | A | 6/1996 | Srisathapat et al. |
| 5,599,326 | A | 2/1997 | Carter |
| 5,683,370 | A * | 11/1997 | Luther et al. ................... 604/528 |
| 5,720,720 | A * | 2/1998 | Laske et al. .................... 604/500 |
| 5,762,637 | A | 6/1998 | Berg et al. |
| 5,820,610 | A | 10/1998 | Baudino et al. |
| 5,848,996 | A * | 12/1998 | Eldor ............................ 604/272 |
| 5,851,203 | A | 12/1998 | van Muiden |
| 5,913,848 | A | 6/1999 | Luther et al. |
| 5,957,910 | A | 9/1999 | Holden, II et al. |
| 6,090,099 | A | 7/2000 | Samson et al. |
| 6,093,180 | A | 7/2000 | Elsberry |
| 6,171,297 | B1 | 1/2001 | Pedersen et al. |
| 6,503,353 | B1 | 1/2003 | Peterson et al. |
| 6,508,789 | B1 | 1/2003 | Sinnott et al. |
| 6,592,587 | B1 * | 7/2003 | Roger ........................... 606/318 |
| 6,676,643 | B2 | 1/2004 | Brushey |
| 6,827,693 | B2 | 12/2004 | White et al. |
| 6,855,124 | B1 | 2/2005 | Gonzalez et al. |
| 6,863,662 | B2 | 3/2005 | Luther |
| 6,893,429 | B2 | 5/2005 | Petersen |
| 6,902,207 | B2 | 6/2005 | Lickliter |
| 6,945,969 | B1 | 9/2005 | Morris et al. |
| 6,991,626 | B2 | 1/2006 | Wantink et al. |
| 7,399,296 | B2 | 7/2008 | Poole et al. |
| 7,641,638 | B2 | 1/2010 | Waxman et al. |
| 7,819,842 | B2 | 10/2010 | Kaemmerer |
| 7,976,530 | B2 | 7/2011 | Johnson et al. |
| 7,988,674 | B2 | 8/2011 | Adams et al. |
| 2002/0095124 | A1 * | 7/2002 | Palasis et al. ................. 604/272 |
| 2003/0032925 | A1 * | 2/2003 | Stone ............................ 604/191 |
| 2003/0153879 | A1 | 8/2003 | Luther |
| 2003/0199831 | A1 | 10/2003 | Morris et al. |
| 2003/0199852 | A1 | 10/2003 | Seward et al. |
| 2004/0044329 | A1 | 3/2004 | Trudell |
| 2004/0087933 | A1 * | 5/2004 | Lee et al. ...................... 604/532 |
| 2004/0215162 | A1 * | 10/2004 | Putz .............................. 604/500 |
| 2005/0043714 | A1 | 2/2005 | Zhou |
| 2005/0137134 | A1 | 6/2005 | Gill et al. |
| 2005/0137535 | A1 * | 6/2005 | Gollobin ....................... 604/263 |
| 2006/0127158 | A1 | 6/2006 | Olson et al. |
| 2006/0129126 | A1 | 6/2006 | Kaplitt et al. |
| 2006/0135945 | A1 | 6/2006 | Bankiewicz et al. |
| 2007/0088295 | A1 * | 4/2007 | Bankiewicz ................... 604/264 |
| 2007/0129663 | A1 | 6/2007 | Bertrand et al. |
| 2007/0276340 | A1 | 11/2007 | Poston et al. |
| 2008/0097287 | A1 | 4/2008 | Nelson et al. |

FOREIGN PATENT DOCUMENTS

| | | |
|---|---|---|
| EP | 0 678 302 B1 | 2/1999 |
| JP | 2005323658 | 11/2005 |
| WO | WO 97/40879 | 11/1997 |
| WO | WO 02/083228 A2 | 10/2002 |
| WO | WO 03/002170 A2 | 1/2003 |
| WO | WO 03/002170 A3 | 3/2003 |
| WO | WO 02/083228 A3 | 4/2003 |
| WO | WO 03/090835 A1 | 11/2003 |
| WO | WO 2007/024841 A2 | 3/2007 |

OTHER PUBLICATIONS

International Search Report and Written Opinion of the International Searching Authority for PCT/US2008/084604; pp. 1-15.

U.S. Appl. No. 11/799,179, filed May 1, 2007, Skakoon.

U.S. Appl. No. 11/799,312, filed May 1, 2007, Johnson et al.

U.S. Appl. No. 11/799,319, filed May 1, 2007, Johnson et al.

U.S. Appl. No. 12/357,120, filed Jan. 21, 2009, Nelson.

"Cable Design Options & Capabilities" datasheet [online]. Polymicro Technologies, LLC, Phoenix, Arizona, 2006 [retrieved on Aug. 15, 2007]. Retrieved from the Internet:<URL:http://www.polymicro.com/catalog/4_8.htm>; pp . 1-2.

Hou et al., "The repair of brain lesion by implantation of hyaluronic acid hydrogels modified with laminin," *J. Neuroscience Methods*, Oct. 15, 2005, 148(1):60-70. Published online Jun. 22, 2005.

"Introduction to Fiber Optics" datasheet [online]. Communications Specialties, Inc., Hauppauge, New York [retrieved on Aug. 29, 2007]. Retrieved from the Internet:<URL:http://www.commspecial.com/fiberguide-print.htm>; pp. 1-7.

Krauze et al., "Real-time imaging and quantification of brain delivery of liposomes," *Pharm. Res.*, Nov. 2006, 23(11):2493-2504. Published online Sep. 14, 2006.

Krauze et al., "Reflux-free cannula for convection-enhanced high-speed delivery of therapeutic agents," *J. Neurosurg.*, Nov. 2005, 103:923-929.

Morrison et al., "Focal delivery during direct infusion to brain: role of flow rate, catheter diameter, and tissue mechanics," *Am. J. Physiol. Regul. Integr. Comp. Physiol.*, Oct. 1999, 277(4):R1218-R1229.

"Optical Fiber Intro" datasheet [online]. Cables Unlimited, Bohemia, New York, 2006 [retrieved on Aug. 29, 2007]. Retrieved from the Internet:<URL:http://www.connectworld.net/syscon/1stanfrm.htm>; pp. 1-6.

Sanftner et al., "AAV2-mediated gene delivery to monkey putamen: Evaluation of an infusion device and delivery parameters," *Exp. Neurol.*, Aug. 2005, 194(2):476-483. Published online Apr. 20, 2005.

"Flexible Fused Silica Capillary Tubing" datasheet [online]. Polymicro Technologies, LLC, Phoenix, AZ, page available Mar. 12, 2005 [retrieved on Mar. 12, 2009]. Retrieved from the Internet:<URL:http://web.archive.org/web/20050312103226/http://www.polymicro.com/products/capillarytubing/products_capillarytubing_tsp_tsg_tsu.htm>; pp. 1-2.

"Thick Wall Flexible Fused Silica Capillary Tubing" datasheet [online]. Polymicro Tecnhologies, LLC, Phoenix, AZ, page available Oct. 18, 2005 [retrieved on Mar. 12, 2009]. Retrieved from the Internet:<URL:http://web.archive.org/web/20051018182636/http://www.polymicro.com/products/capillarytubing/products_capillarytubing_tsp.htm>; pp. 1-2.

\* cited by examiner

*Fig. 3A* *Fig. 3B*
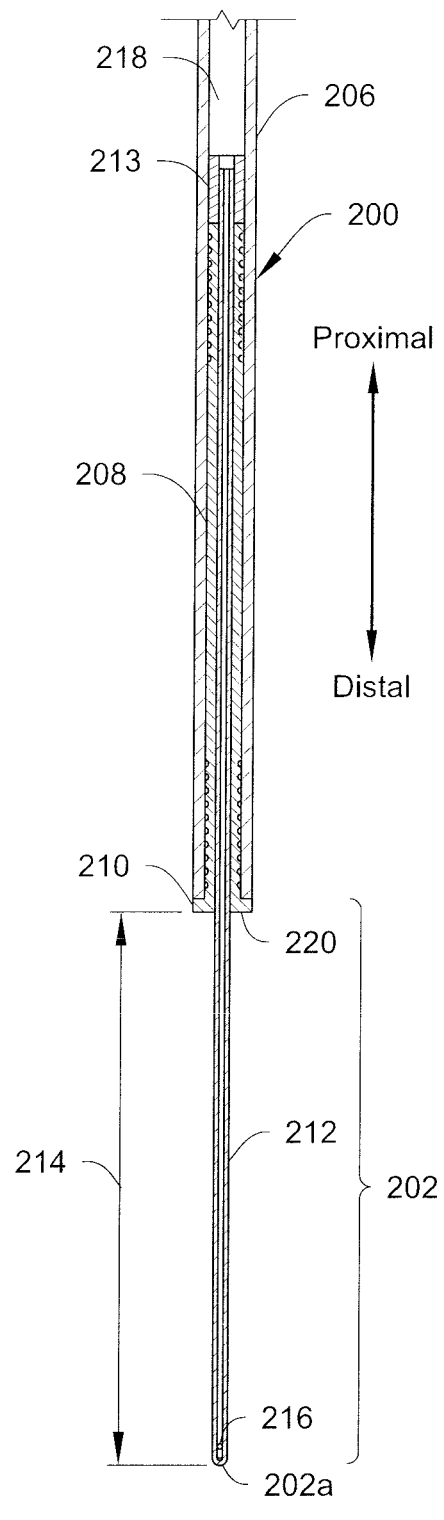
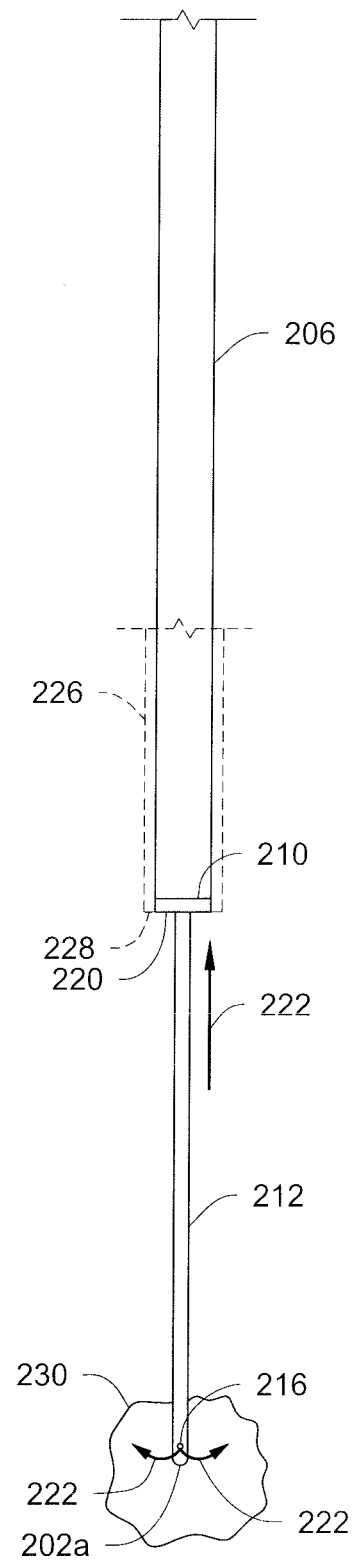

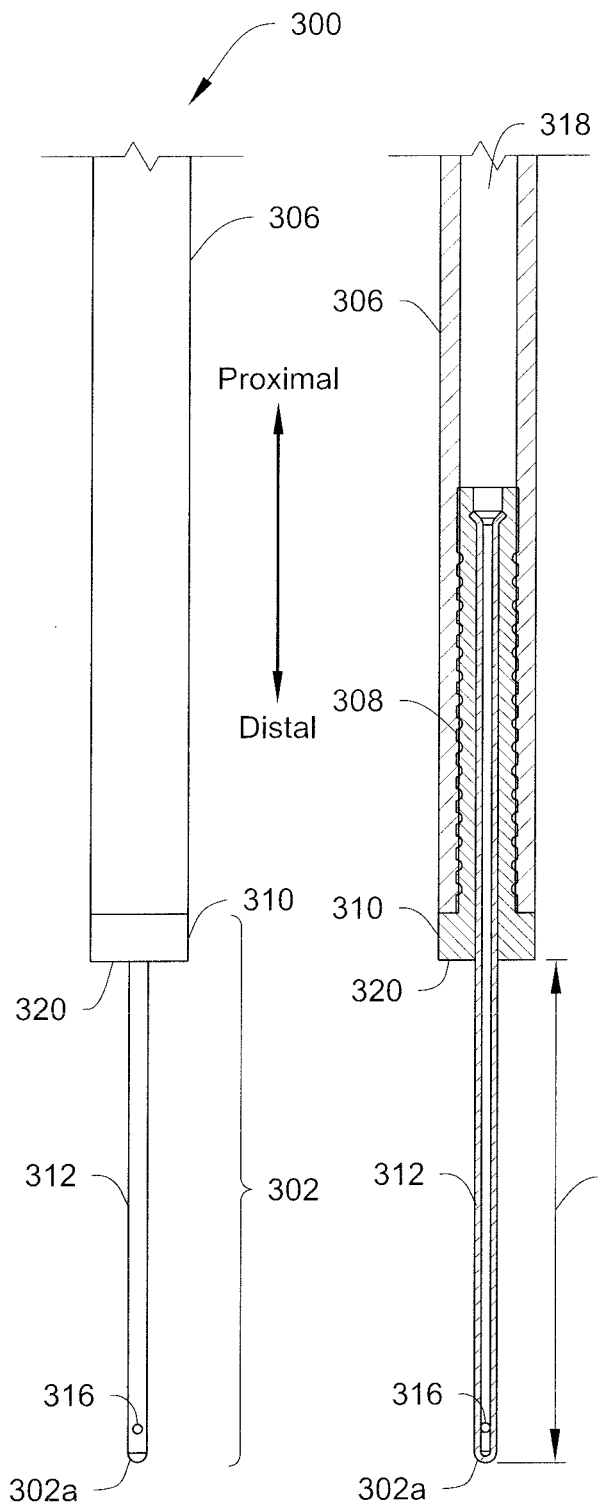
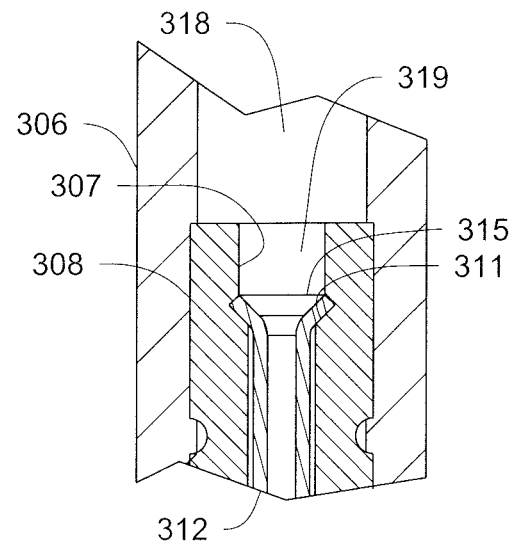
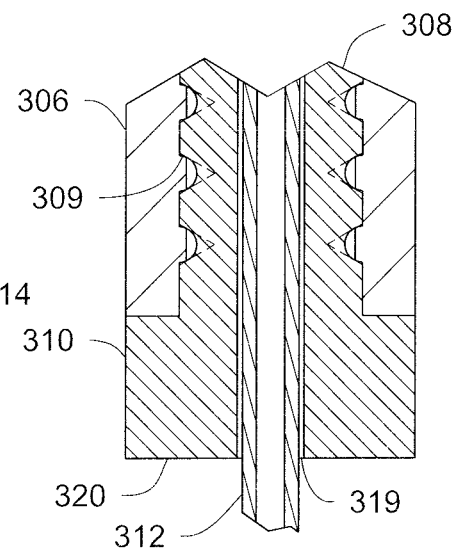

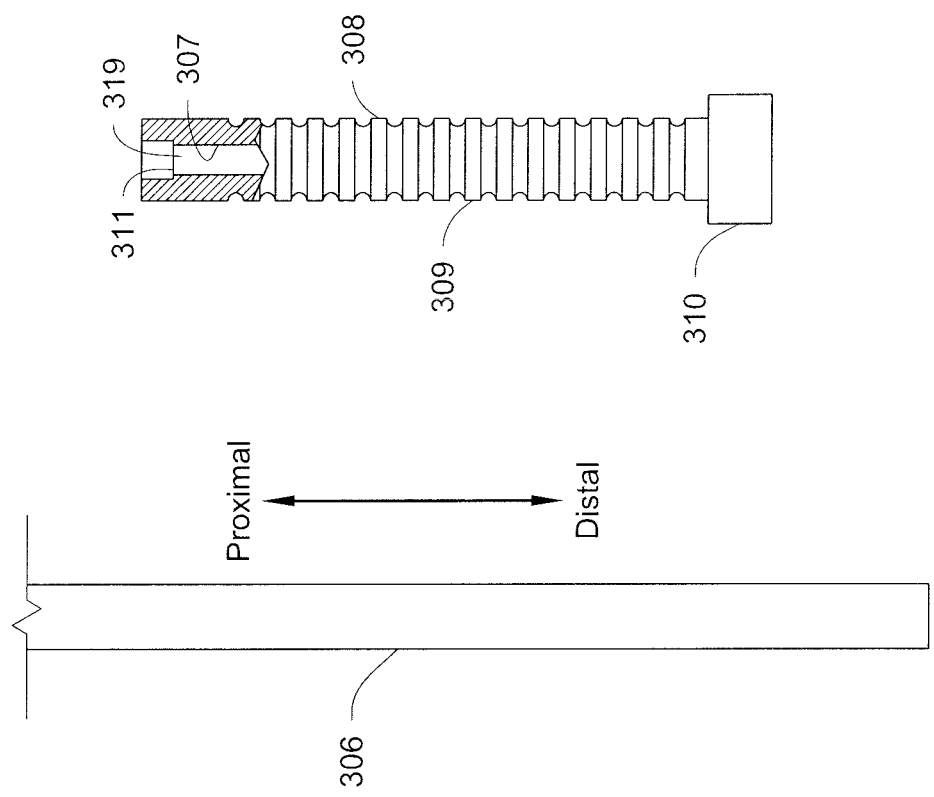
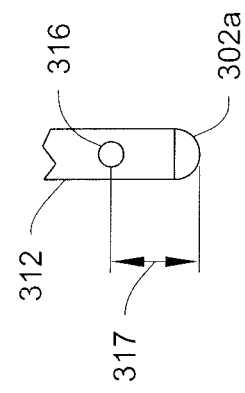
Fig. 7B
Fig. 7C
Fig. 7A
Fig. 6
Fig. 5

Fig. 10A
Fig. 10B
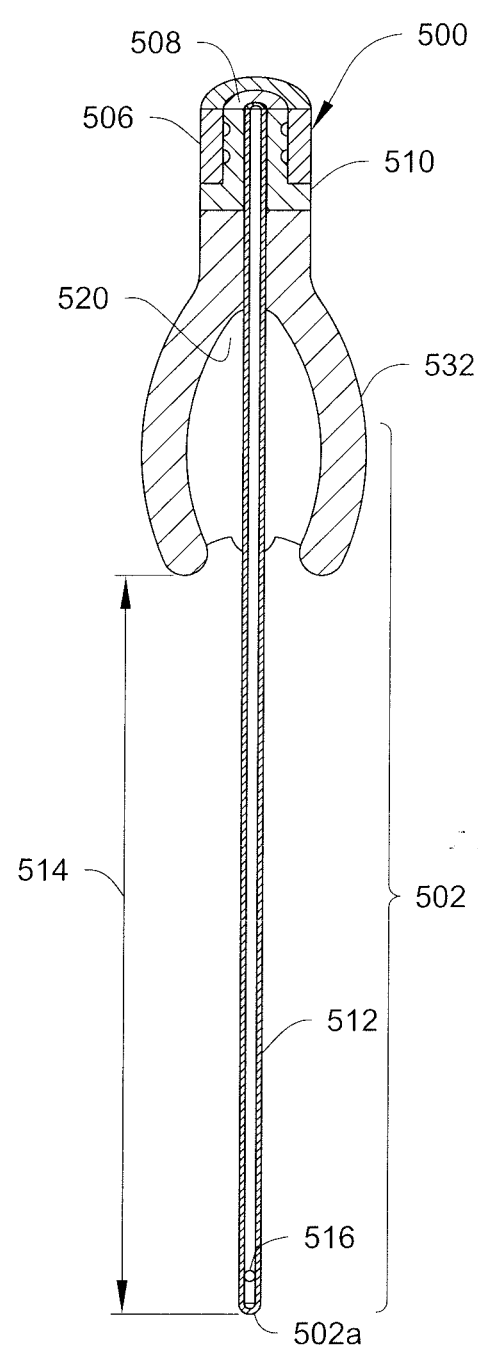
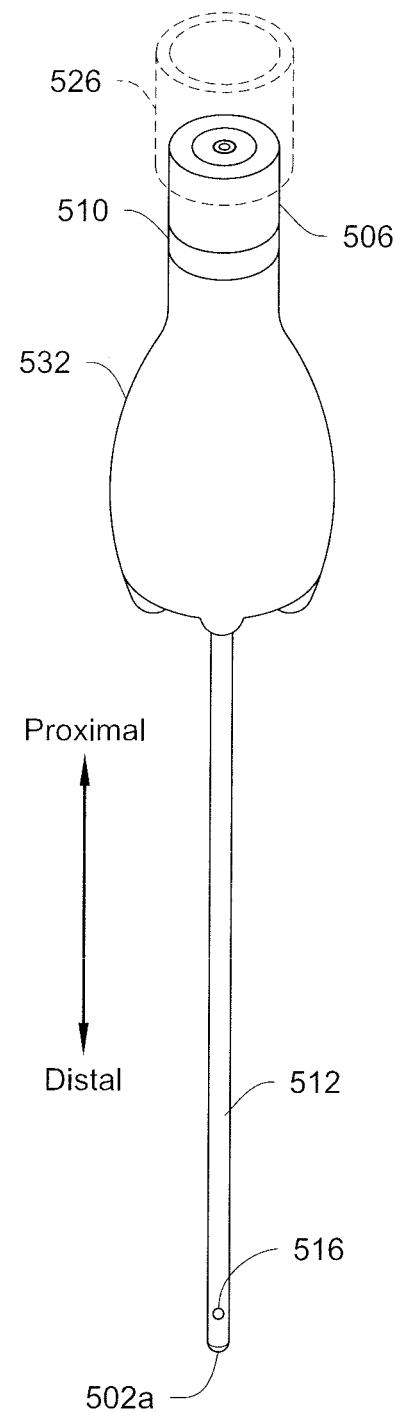

Fig. 11A
Fig. 11B
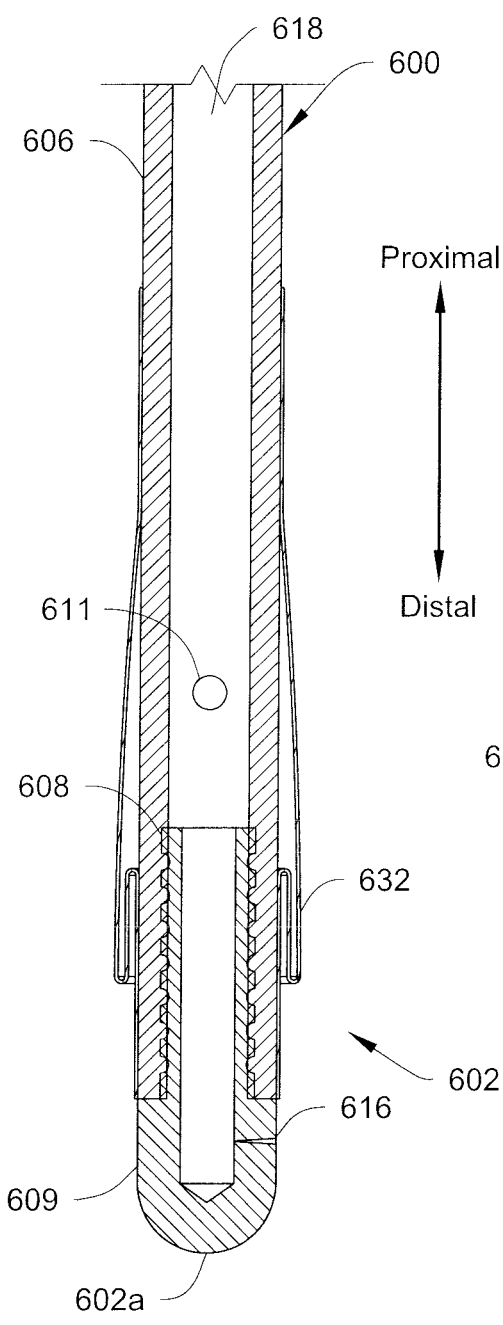
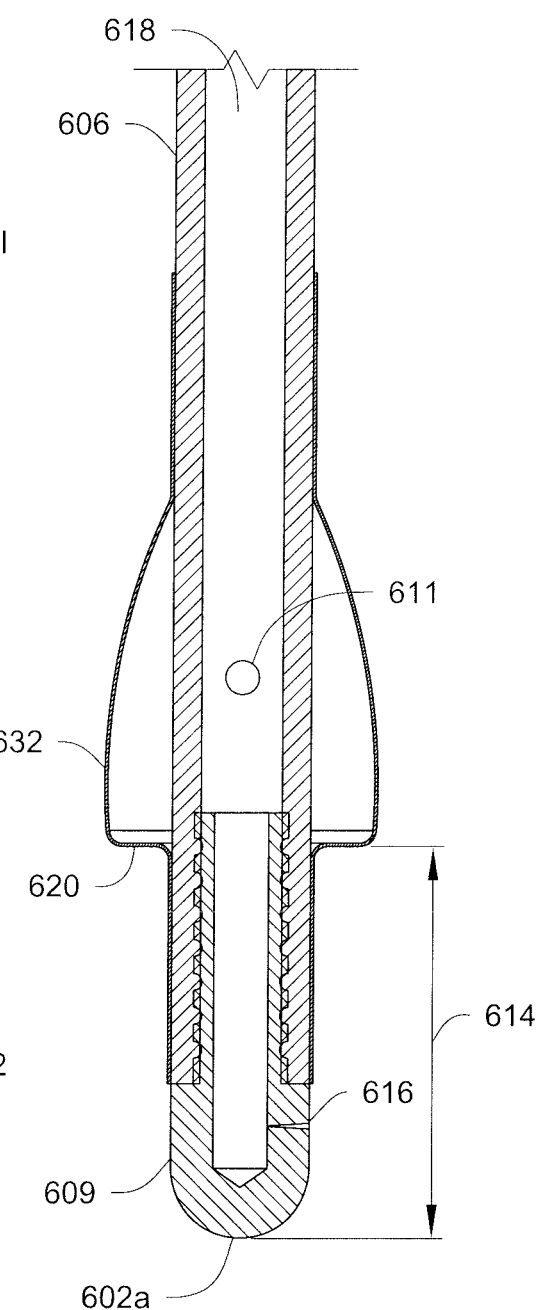

INFUSION CATHETER ASSEMBLY WITH REDUCED BACKFLOW

RELATED APPLICATION(S)

The present application claims the benefit of U.S. Provisional Pat. App. No. 61/005,047, filed 30 Nov. 2007, the contents of which are incorporated by reference herein in their entirety.

TECHNICAL FIELD

The present invention relates generally to medical devices and, more particularly, to infusion devices (e.g., intraparenchymal catheters), and to systems and methods for making and using a catheter assembly.

BACKGROUND

Medical procedures involving access to the brain through a burr hole in the skull are used to treat a variety of medical conditions. For example, burr holes may be formed to allow implantation of a catheter, e.g., an intraparenchymal (IPA) catheter, to deliver a therapeutic agent (infusate) to a target tissue region within a mammalian brain for the treatment of neurological ailments.

Use of an IPA catheter to deliver a therapeutic agent to the brain generally involves the insertion of the catheter into the brain and dispensing the agent at the desired target region. During a typical implantation procedure, an incision may be made in the scalp to expose the patient's skull. After forming a burr hole through the skull, the catheter may be inserted into the brain. To accurately place the catheter and avoid unintended injury to the brain, surgeons typically use stereotactic apparatus/procedures. One exemplary stereotactic apparatus is described in U.S. Pat. No. 4,350,159 to Gouda, which may be used to position, for example, an electrode. A cannula or needle may be located and held with the stereotactic equipment, after which the catheter may be inserted through the cannula. Once a distal tip of the IPA catheter is correctly located, the cannula may be removed, leaving the catheter in place.

While effective for delivering substances to the desired location in the body, care must be taken during implantation and therapy delivery to ensure that backflow of the therapeutic agent is minimized. "Backflow," as used herein, refers to portions of the therapeutic agent delivered by the delivery tube (e.g., catheter) that tends to flow back along the outer diameter of the body of the delivery tube (e.g., towards its proximal end) instead of infusing into the intended target tissue region surrounding the distal tip of the catheter.

While the degree of backflow may vary, it may become severe if the infusate finds a path into the Cerebral Spinal Fluid (CSF). If such a path is formed, the infusion pressure may drop dramatically (e.g., until it equals CSF pressure).

In addition to reducing the efficacy of the treatment (e.g., less than the desired volume of therapeutic agent is delivered to the intended target tissue region), backflow may further result in substance delivery to unintended regions of the body, e.g., other regions along the catheter length. Moreover, the volume of substance that backflows is basically wasted, a consequence which is particularly undesirable when the therapeutic agent is expensive or otherwise difficult to obtain.

Many conventional catheters are furthermore designed for treatment of acute conditions. As a result, they are often configured for temporary implantation and are frequently constructed of generally rigid materials that are not amenable to modification (e.g., trimming) during the actual implant procedure as may be required for longer term implantation. The ability to modify the catheter length would be advantageous for implantation of catheters associated with long term (chronic) therapy.

SUMMARY

The present invention may overcome these and other issues by providing catheter assemblies, systems, and methods operable to introduce an agent into the body while reducing the occurrence of backflow of the agent along the catheter assembly track. Catheter assemblies in accordance with embodiments of the present invention may also be constructed of trimmable materials so that they may be cut to the desired length during the implantation procedure. In one embodiment, a catheter assembly is provided having a flexible tubular catheter body. The body has proximal and distal ends and includes an inner surface defining a lumen extending between the proximal and distal ends. A rigid tubular needle is also provided. The needle is partially located within the lumen of the body and extends outwardly from the distal end of the body. The needle includes a nonporous outer surface defined by a diameter that is less than a diameter of an outer surface of the body; and a proximal end having a flange with a diameter larger than the diameter of the outer surface of the needle. The flange may be fixed relative to the inner surface of the body. The needle also includes a sealed distal tip located a preset distance beyond the distal end of the body. The needle defines a side flow aperture formed along the outer surface of the needle and proximate to, but offset from, the sealed distal tip. The side flow aperture is in fluid communication with the lumen of the body.

In another embodiment of the present invention, a catheter assembly is provided having a flexible tubular catheter body with proximal and distal ends. The body includes an inner surface defining a lumen extending between the proximal and distal ends. A guide tube is provided and fixed to the inner surface of the body near the distal end of the body. A tubular needle is also provided and fixed to an inner surface of the guide tube such that it extends outwardly from a distal end of the guide tube. The needle includes an outer surface defined by a diameter that is less than a diameter of an outer surface of the body; and a sealed distal tip located a preset distance beyond the distal end of the guide tube. The needle further defines at least two side flow apertures formed along the outer surface of the needle proximate to, but offset from, the sealed distal tip. The side flow apertures are in fluid communication with the lumen of the body.

In still another embodiment of the invention, a method for delivery of a therapeutic substance to a target tissue region in a patient's brain is provided. The method includes implanting into the target tissue region a distal end of a tubular needle of a catheter assembly. The catheter assembly includes a flexible tubular catheter body having proximal and distal ends, the body having an inner surface defining a lumen extending between the proximal and distal ends; and a guide tube fixed to the inner surface of the body near the distal end of the body. The assembly also includes the tubular needle. The tubular needle is fixed to an inner surface of the guide tube and extends outwardly from a distal end of the guide tube. In one embodiment, the tubular needle includes: an outer surface defined by a diameter that is less than a diameter of an outer surface of the body; and a sealed distal tip located a preset distance beyond the distal end of the guide tube. The needle defines at least two side flow apertures formed along the outer surface of the needle proximate to, but offset from, the sealed distal tip, the side flow apertures in fluid communication with the lumen of the body. The method further includes infusing the therapeutic substance into the target tissue region through the lumen at a constant flow rate via convection enhanced delivery from the side flow apertures.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 1A-1B illustrate enlarged views of a distal end of a diagrammatic catheter (e.g., IPA catheter), wherein: FIG. 1A illustrates a desired or normal distribution of therapeutic agent from a catheter during convection-enhanced delivery (CED); while FIG. 1B illustrates distribution when backflow occurs;

FIGS. 2A-2B illustrates an implanted infusion system in accordance with one embodiment of the present invention, the system including an exemplary IPA catheter or catheter assembly having a distal tip for delivering a therapeutic agent to a body, e.g., to the brain, wherein: FIG. 2A illustrates the IPA catheter implanted within the body; and FIG. 2B illustrates the catheter removed from the body;

FIGS. 3A-3B illustrate the IPA catheter of FIGS. 2A-2B, wherein: FIG. 3A illustrates a partial section view of a distal portion of the catheter; and FIG. 3B illustrates an enlarged partial side elevation view of the distal portion;

FIGS. 3C-3E illustrate a variation of the IPA catheter embodiment of FIGS. 3A-3B, wherein: FIG. 3C illustrates an exploded side elevation view; FIG. 3D illustrates a section view of the catheter as assembled; and FIG. 3E illustrates an enlarged section view of a portion of the catheter;

FIGS. 4A-4D illustrate an IPA catheter in accordance with another embodiment of the invention, wherein: FIG. 4A is a partial side elevation view of the catheter; FIG. 4B is a similar view in section illustrating a guide tube of the catheter; and FIGS. 4C and 4D are enlarged portions of the section view of FIG. 4B illustrating a proximal and a distal end, respectively, of the guide tube;

FIG. 5 is a side elevation view of a catheter body of the catheter of FIGS. 4A-4D;

FIG. 6 is a enlarged and partial cut-away view of the guide tube of the catheter of FIGS. 4A-4D;

FIGS. 7A-7C illustrate a needle of the catheter of FIGS. 4A-4D, wherein: FIG. 7A is a side elevation view; FIG. 7B is an enlarged view of a proximal end of the needle; and FIG. 7C is an enlarged view of a distal end of the needle;

FIGS. 10A-10B illustrate an IPA catheter in accordance with another embodiment of the invention, wherein: FIG. 10A illustrates a partial perspective section view of a distal portion of the catheter; and FIG. 10B illustrates an enlarged partial perspective view of the distal portion;

FIGS. 11A-11B illustrate an IPA catheter in accordance with yet another embodiment of the invention, wherein: FIG. 11A illustrates a section view of a distal portion of the catheter with a balloon of the catheter deflated; and FIG. 11B illustrates generally the same view with the balloon inflated;

Figure 1A:
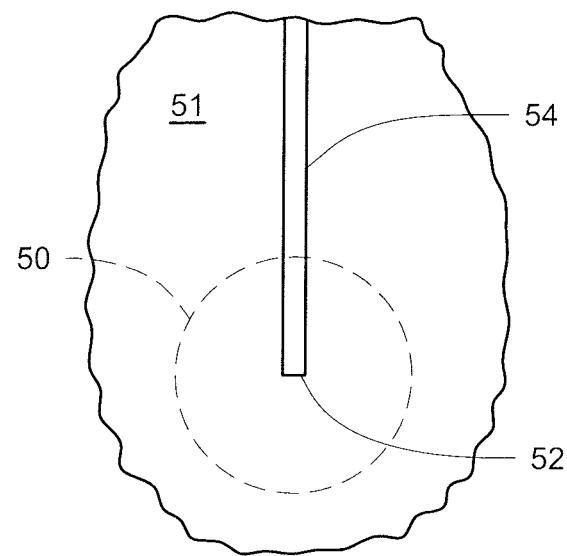

The figures are rendered primarily for clarity and, as a result, are not necessarily drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the present invention are directed generally to fluid conduits such as infusion catheter assemblies (also be referred to herein merely as "catheters") and to systems and methods for using the same. For example, embodiments of the present invention may include a delivery tube, e.g., IPA catheter, for delivering a therapeutic agent to a region of the body. As further described below, embodiments of the present invention may reduce backflow of the therapeutic agent along the delivery track of the delivery tube/catheter body, thus delivering a precise, predetermined volume of therapeutic agent to a target tissue region of the body. Other embodiments of the invention may be directed to methods for making such catheter assemblies.

Figure 1B:
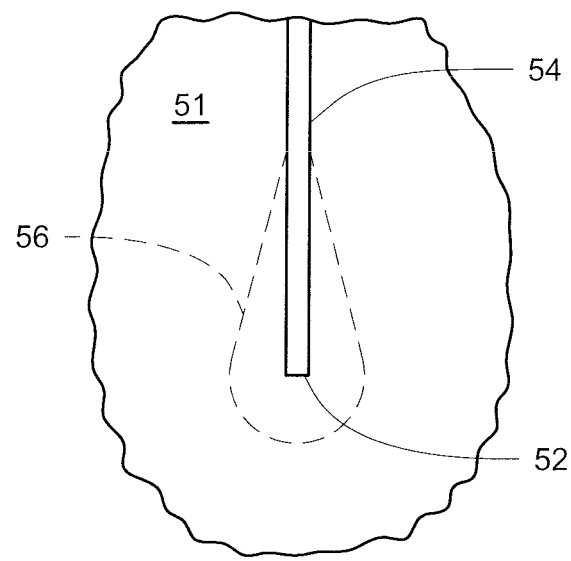

Backflow may occur when a fluidic seal between the delivery tube and surrounding tissue is broken. To illustrate backflow, FIG. 1A shows a desired spherical distribution 50 of a substance into tissue 51 from an axial distal end 52 of a catheter 54, while FIG. 1B illustrates a "tear-drop" distribution 56 that may occur when a catheter experiences backflow. Although somewhat difficult to measure directly, backflow may be detected by observation of substance dispersion under, for example, magnetic resonance imaging (MRI). While backflow may occur with many delivery techniques, it may be particularly problematic during convection enhanced delivery (CED) in the treatment of target tissue within mammalian brains. Convection enhanced delivery (CED) to the brain uses bulk flow in the extracellular space that results from a pressure gradient to significantly enhance tissue penetration of the delivered substance.

In some embodiments of the present invention, catheters are provided that include a distal end having flow openings or apertures oriented at an angle that is skewed relative to (or otherwise nonparallel to) a longitudinal axis of the distal portion of the catheter. As a result, the catheter may be configured such that fluid exiting the catheter does so in a nonaxial manner, e.g., at an angle of about 90 degrees to a longitudinal axis of the distal portion of the catheter.

In some embodiments, the nonaxial apertures may be provided by a tip member, e.g., insert, that fits within the distal end of the catheter body and effectively blocks axial flow. The flow apertures may then be formed on an outer surface of the insert. In other embodiments, the tip member may be a closed- or sealed-end needle secured relative to the distal end of the catheter body. The needle may then define side flow apertures as further described below. The apertures may be offset a slight distance from the most distal end of the catheter (e.g., from the distal end of the insert or needle) as shown in the figures and described below. These side flow openings are believed to assist with reducing backflow along the delivery track of the catheter.

In still other embodiments, the catheter may include an obstructive element positioned along the body of the catheter and spaced away from the distal end/flow openings by a preset distance. The obstructive element may interfere with the flow of fluid (e.g., therapeutic agent) back along the catheter delivery track.

Catheters in accordance with embodiments of the present invention may also provide a catheter body that may be easily trimmed, e.g., sheared, to the correct length during the implantation procedure. That is, catheters in accordance with embodiments of the present invention may include a body that is made from a material that is shearable or trimmable. A catheter that is "shearable" or "trimmable," as these terms are used herein, may be cleanly cut via a shearing or scissoring action without the use of mandrels or secondary tools and without damaging the catheter body itself (e.g., occluding the lumen, splintering or weakening of the catheter material). The ability to trim the proximal end of the catheter is beneficial to implantations for chronic treatment as it allows the surgeon to easily and accurately size the catheter length during the implantation procedure.

Figure 2A:
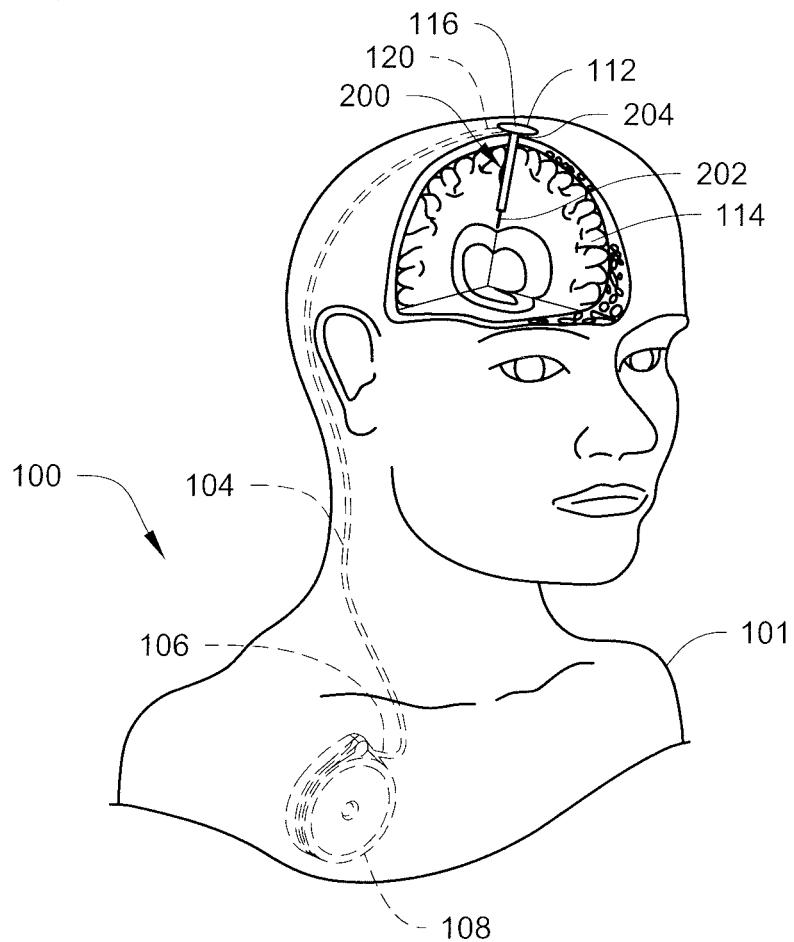
Figure 2B:
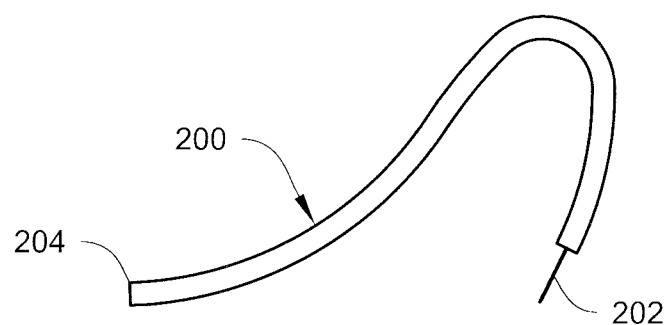

FIG. 2A illustrates an exemplary implantable medical system (e.g., a brain infusion catheter system 100) that may utilize an IPA catheter 200 in accordance with one embodiment of the present invention. FIG. 2A illustrates the IPA catheter implanted within the body, while FIG. 2B illustrates the catheter removed from the body. While shown as part of a completely implanted system, applications where a portion of the catheter 200 is external to the body are also contemplated.

The illustrated infusion system may include a first medical tube, e.g., the IPA catheter or catheter assembly 200, and an optional second medical tube, e.g., delivery catheter 104. The delivery catheter 104 may have an end 106 coupled to a reservoir containing a volume of a therapeutic agent (e.g., an infusion pump 108, which may be identical or similar to the SynchroMed® II programmable infusion pump distributed by Medtronic, Inc., of Minneapolis, Minn. USA). In the illustrated embodiment, the pump 108 is implanted within the body 101. However, external reservoirs, e.g., external pumps, syringes, drip bags, etc., may also be used.

The IPA catheter 200 may have its distal portion 202 implanted, via a burr hole 112, at a predetermined location within the body 101, e.g., brain 114, of the patient. In some embodiments, a burr hole anchor 116 may be used to secure a proximal end 204 of the catheter 200 relative to the cranium and permit connection to a corresponding proximate end 120 of the delivery catheter 104. Thus, the pump 108 may be fluidly coupled to the catheter 200.

The system 100 may, in one embodiment, be configured to deliver a therapeutic agent for the treatment of chronic brain and central nervous system disorders, e.g., Huntington's disease. The therapeutic agent may be delivered, via the catheter assembly 200 (or 200', 300, 400, 500, 550, 600, or 700 as described below), from the pump 108 to the brain 114. This application is not limiting, however, as the system may be configured to deliver other therapeutic agents either to the brain (e.g., such as agents for the treatment of Parkinson's or Alzheimer's disease) or to most any other area of the body without departing from the scope of the invention.

It is noted that the terms "comprises" and variations thereof do not have a limiting meaning where these terms appear in the accompanying description. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

With this general overview, the following description will address various catheter embodiments, as well as methods for making and using the same. While these embodiments may be described with some degree of specificity, they are nonetheless intended to be exemplary. Those of skill in the art will recognize that other embodiments are possible without departing from the scope of the invention.

FIGS. 3A and 3B illustrate enlarged views of a distal portion 202 of the exemplary IPA catheter 200 of FIGS. 2A and 2B. FIG. 3A illustrates a section view of the distal portion 202, while FIG. 3B illustrates a similar side elevation view.

The catheter 200 may include a flexible tubular catheter body 206. In one embodiment, the body 206 is constructed of an elastomeric, homogeneous, and shearable material. An optional insert, e.g., annular guide member or tube 208, may be attached to the body (e.g., to an inner surface of a bore or lumen 218 of the body 206) near the body's distal end. In one embodiment, the guide tube is bonded to the catheter body. For instance, in one embodiment, the guide tube is reflow bonded to the catheter body. In another embodiment, the guide tube is bonded to the catheter body with an appropriate adhesive selected to adhere the tube to the catheter body and to maintain adhesion while the catheter assembly is implanted in the target tissue region. However, these configurations are not limiting. As shown in FIGS. 3A and 3B, the guide tube 208 may include a flange or flange portion 210 that abuts the distal end of the body 206 when the guide tube 208 is fully inserted. The guide tube may further include a grooved or roughened outer surface (described in more detail with respect to the guide tube 208' below) to facilitate bonding with the catheter body.

A rigid and hollow tubular tip member may be partially located within the lumen 218 of the body 206 and extend outwardly from its distal end. In the illustrated embodiment, the tip member is a nonporous tube or needle 212. The needle 212 may be fixed or otherwise bonded to the guide tube 208 such that it extends beyond the distal end of the guide tube as illustrated in FIG. 3A. In one embodiment, the needle 212, e.g., its distal tip 202a, is configured to extend a preset distance 214 beyond the distal end of the body 206 and guide tube 208 (e.g., beyond the flange 210 of the guide tube) for reasons that are further explained below.

The distal tip or end 202a of the needle 212 (which forms the most-distal end of the catheter 200) may be sealed or closed (e.g., rounded) as shown in FIG. 3B. This axial closure of the needle prevents axial flow from the needle tip. However, the needle 212 may include one or more flow openings or apertures offset from the sealed distal tip 202a, the openings each having an axis that forms an angle other than zero degrees with a longitudinal axis of the catheter body/needle. For instance, one or more side flow openings 216 each having an axis that forms an angle of about 90 degrees with (e.g., is normal to) the longitudinal axis of the needle may be provided. These side flow openings are fluidly coupled to the lumen 218 of the catheter body so that therapeutic substance flowing through the lumen may pass into the lumen of the needle 212 and out through the opening(s) 216.

The configuration of the catheter 200 provides several benefits. For instance, by utilizing a closed end 202a, the catheter may be inserted into the body with little or no tissue coring. In addition to reduced coring, the relatively smaller (compared to the catheter body) diameter of the protruding needle 212 minimizes the diameter of the most distal portion of the catheter 200, which may reduce tissue trauma during catheter introduction. The smaller diameter of the needle 212 may further contribute to reduced backflow as increased backflow has been associated with increased diameter of the catheter, as well as with increased infusate flow rate (see, e.g., Morrison et al., *Focal Delivery During Direct Infusion to Brain; Role of Flow Rate, Catheter Diameter, and Tissue Mechanics*, Am J Physiol Regul Integr Comp Physiol 277, R1218-R1229 (1999)).

Moreover, by utilizing side flow opening(s) 216, the infusion peak pressure may potentially be reduced (as compared to an axial flow catheter), which may further reduce backflow. Still further, the side flow opening(s) may, in some embodiments, be relatively small, reducing the opportunity for tissue in-growth.

The catheter 200 may further provide an obstructive element, e.g., ledge 220, positioned along the catheter and spaced apart from the distal tip and side flow openings by a preset distance. The ledge may, in one embodiment, be formed by the flange 210 of the guide tube 208 positioned at or near the distal end of the body such that the ledge is normal to a longitudinal axis of the guide tube and/or needle. The ledge 220 may form a barrier capable of interfering with backflow 222 of therapeutic substance delivered by the catheter 200. For example, any volume of substance 222 that tends to flow into any low pressure void existing between the needle 212 and the surrounding tissue and towards the proximal end of the catheter 200 may be obstructed by the radially protruding ledge 220 as represented in FIG. 3B.

While not wishing to be bound to any particular configuration, the catheter body 206 (like the other catheter bodies described herein) may, in one embodiment, be made from a shearable material such as 80 Shore A durometer urethane and have an inner surface defined by an inner diameter of about 0.024 inches (in) and an outer surface defined by an outer diameter of about 0.041 in. As a result, the proximal end of the catheter body may be cut (e.g., shear cut), during the implantation procedure, to provide the catheter with the desired length. While described as urethane, the catheter body 206 may be made from other materials such as other urethanes, silicones, and blends of the same.

The guide tube 208, on the other hand, may be made from a material that is substantially more rigid than the material of the body, e.g., polyetheretherketone (PEEK) or 316 stainless steel. In the illustrated embodiment, the guide tube may have a length (including the flange 210) of about 0.2 in to about 0.5 in, e.g., about 0.4 in. However, relative size of the guide tube, as well as the other components of the catheter, may be adapted to suite most any particular application.

The needle 212 may, in one embodiment, be made from 316 stainless steel hypodermic tubing and have a proximal end that is fixed, when assembled, at a location within the lumen of the body 206 and located at or near the proximal end of the guide tube (or the optional sleeve 213 when the latter is included). The needle 212 may further have an inner surface defined by a diameter of about 0.004 in, and an outer surface defined by a diameter of about 0.006 in to about 0.010 in, e.g., about 0.008 in (e.g., a 33 gage needle). Accordingly, the diameter of the outer surface of the needle 212 is less than the diameter of the outer surface of the body 206. In some embodiments, a ratio of the diameter of the outer surface of the tubular catheter body 206 to the diameter of the outer surface of the needle may be about 4:1 to about 6:1, e.g., about 5:1.

In the illustrated embodiment, the one or more side flow openings 216 may have a diameter of about 0.004 in. Moreover, the needle 212 may be bonded to the guide tube 208 with a cyanoacrylate adhesive. In another embodiment (see FIG. 3A), the sleeve 213 may be provided. The sleeve 213 may be bonded to a proximal end of the guide tube 208 and also to the needle 212, thereby securing the needle relative to the guide tube. In yet other embodiments, the needle could be overmolded with the guide tube, negating the need for the sleeve 213.

Once again, while identified herein with some degree of specificity, the sizes, materials, and geometry of various components are understood to be exemplary only and other sizes, materials, and geometries are certainly possible without departing from the scope of the invention.

Figure 3C:
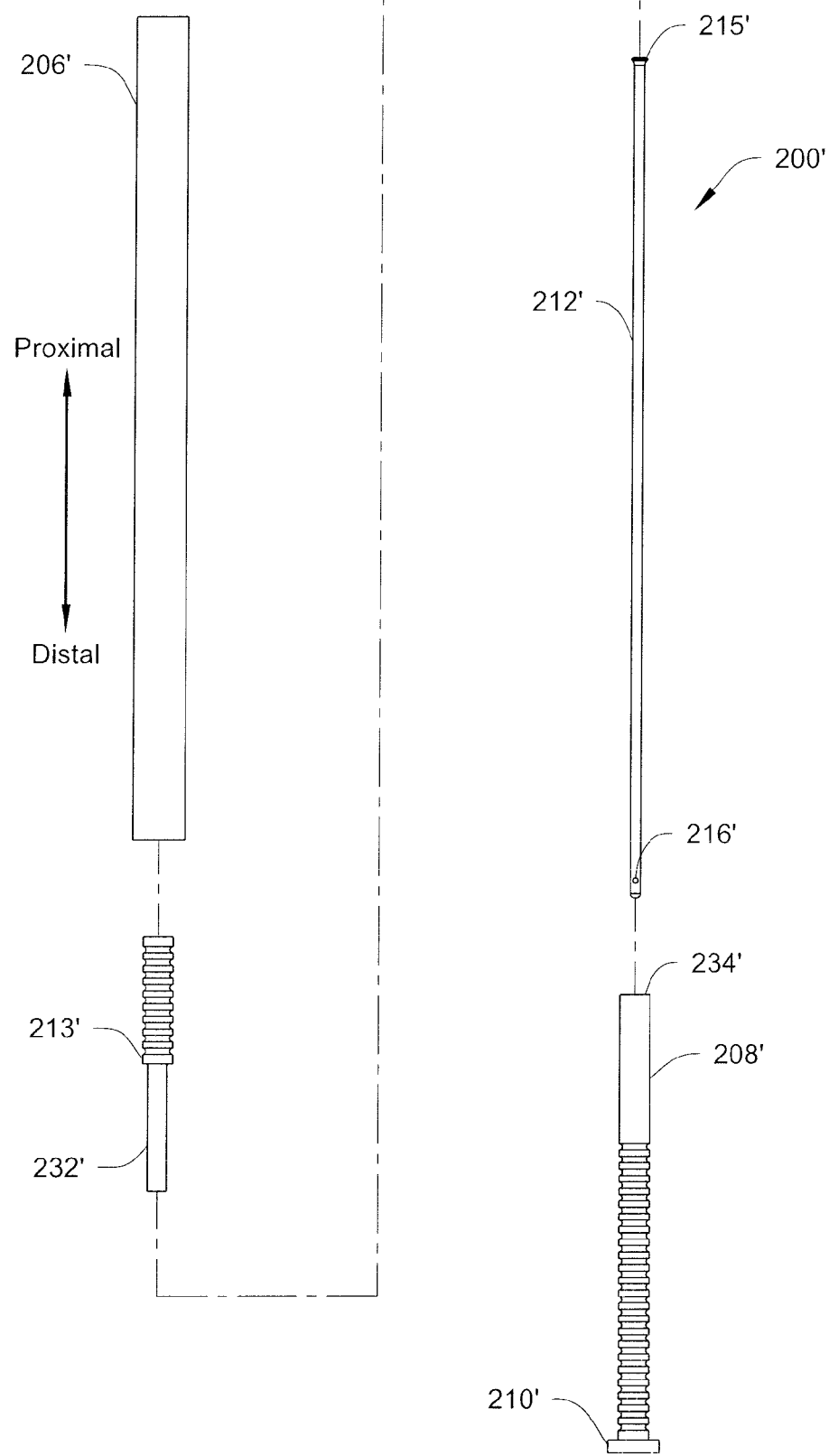
Figure 3D:
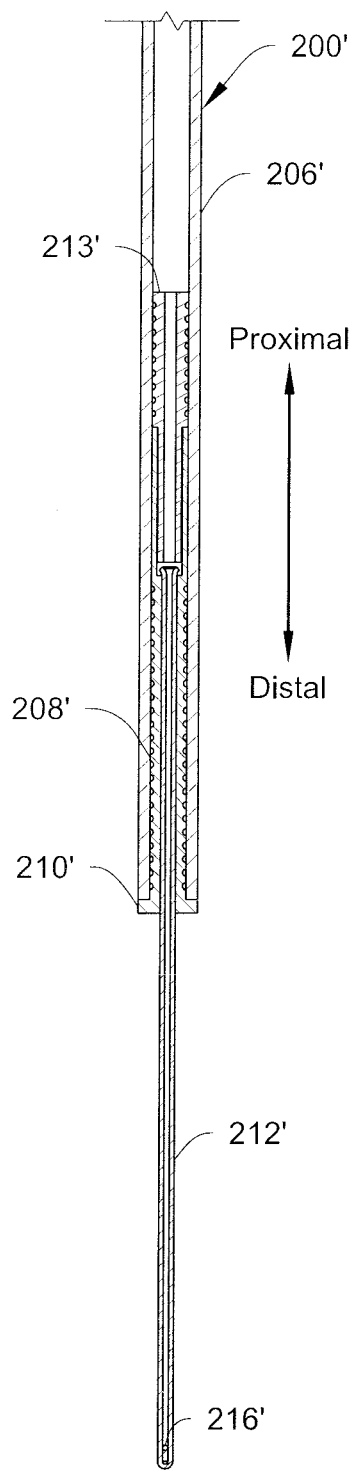
Figure 3E:
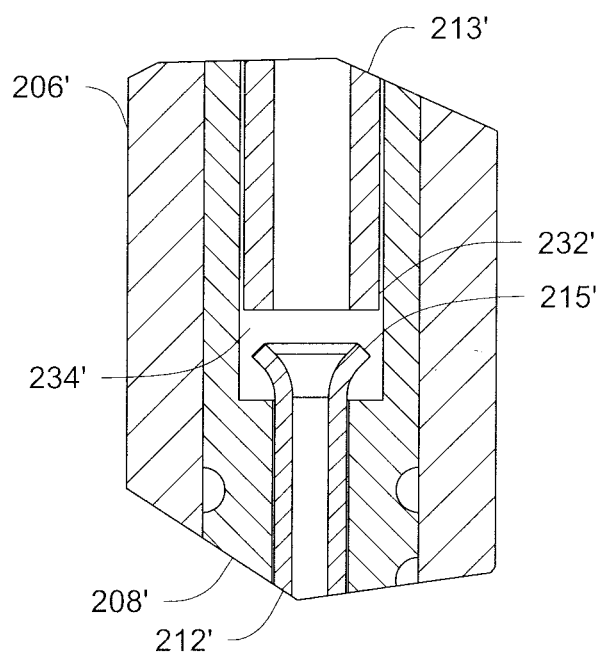

In yet other embodiments, a catheter 200' similar to the catheter 200 may be provided as shown in FIGS. 3C-3E. In this particular embodiment, identified components may be substantially similar or identical to the like components of the catheter 200 except as otherwise described and/or illustrated herein.

As shown in FIG. 3C, the catheter 200' may include a body 206', a guide tube 208' forming a flange 210', a spacer 213', and a needle 212' having a nonaxial opening 216'. Unlike the needle 212, however, the proximal end of the needle 212' may be flanged, e.g., form a flange 215' having a diameter larger than the diameter of the outer surface of the remainder of the needle. As a result, the needle 212' may be fed through the guide tube 208' after which the flange 215' may seat near or against a portion (e.g., a land) of the lumen of the guide tube near its proximal end as shown in FIGS. 3D and 3E.

The spacer 213' may be positioned within the catheter body 206' such that a male portion 232' slides into a female portion 234' of the guide tube 208' as shown in FIGS. 3D and 3E. The spacer 213' may thus be used to trap or otherwise mechanically secure the needle in place relative to the catheter body 206'. The catheter body 206' may then be reflowed (heat) bonded to both the guide tube 208' and spacer 213' to yield the assembly of FIG. 3D.

FIG. 3E illustrates an enlarged view of the guide tube 208', the spacer 213', and the flange 215' of the needle 212'. As illustrated in this view, there may be a small, e.g., 0.003-0.004 in, gap between the distal end of the spacer 213' and the bottom of the female portion 234' of the guide tube 208'. Accordingly, the needle 212' may be permitted some slight axial movement. In other embodiments, however, the spacer 213' could be positioned to press the needle 212' against the guide tube 208'.

In most other respects, the catheters 200 and 200' are similar. For instance, they may both have a preset distance 214 (e.g., the distance that the needle 212 extends beyond the flange 210) of about 0.2 in to about 0.5 in), e.g., about 0.4 in. By providing a needle 212 (or 212') that protrudes from and beyond a distal end of the catheter body 206 (or 206') as shown and described, the catheter may be implanted using a cannula 226 (see FIG. 3B) having a distal end 228 that is positionable, e.g., by stereotactic equipment, a distance equal to the preset distance 214 away from the target region 230. As a result, when the catheter 200 is implanted through the cannula, the relatively narrow needle 212 is all that penetrates tissue beyond the distal end 228 of the cannula, i.e., there is no need to force the wider flange 210 and body 206 through the tissue near the target region.

While exemplary needles 212 and 212' are described as having particular lengths, such specific dimensions are not limiting. Rather, the distance 214, e.g., the length of the needle 212, may vary depending on the particular application. For instance, a longer needle may be beneficial in some applications as longer needles may provide increased flow rate for a given needle diameter. Similarly, shorter needles may also be appropriate in some applications.

FIGS. 4A-8 illustrate enlarged views of a distal portion 302 of an IPA catheter or catheter assembly 300 in accordance with another embodiment of the invention. The catheter 300 may be used in place of the catheters 200 and 200' in the system 100 of FIGS. 2A and 2B. Moreover, relative dimensions, materials, etc. described with respect to the catheters 200 and 200' may also apply the catheter 300 unless otherwise noted herein.

FIG. 4A illustrates a side elevation view of the distal portion 302 of the catheter 300, while FIG. 4B illustrates a similar view in section. Once again, the catheter 300 may include a flexible and shearable tubular catheter body 306 having an inner surface and an outer surface, wherein the inner surface defines a lumen 318 extending between the body's proximal and distal ends in a manner generally identical to the bodies (e.g., 206 and 206') already described herein. A tubular insert, e.g., annular guide member or tube 308, may be fixed or otherwise secured relative to the body (e.g., fixed to the inner surface of the lumen 318 of the body 306) near the body's distal end such that a proximal end of the guide tube is intermediate the proximal and distal ends of the body. In one embodiment, the guide tube is bonded e.g., reflow bonded, to the catheter body as further described below. However, such a configuration is not limiting.

As shown in FIGS. 4A-4D, the guide tube 308 may include a distal end having a flange or flange portion 310 that extends beyond the distal end of the body 306 and may abut the same when the guide tube is fully inserted in the body.

In addition to the flange portion, the guide tube 308 may also form a sleeve or sleeve portion having an inner surface and an outer surface. The outer surface 309 may be smooth or, alternatively, define one or more grooves (e.g., circumferential grooves) as shown in FIG. 4D. While illustrated as incorporating grooves of generally semi-circular cross section, this shape is not limiting as grooves of other shapes (e.g., grooves of V-shaped cross section as shown in broken lines in FIG. 4D) are also possible without departing from the scope of the invention. In still other embodiments, the surface 309 may merely be abraded or roughened. Such configurations may facilitate securing of the guide tube 308 to the catheter body 306, e.g., by forming mechanical capture points or recesses into which inwardly extending portions of the body may extend as shown in FIG. 4D. The inner surface 307 of the guide tube 308 (see the enlarged view of the proximal end of the guide tube shown in FIG. 4C) may be defined by a bore 319 extending through the guide tube. In one embodiment, the bore may be a stepped bore forming a recessed land 311 to receive and contact a flange 315 of a needle as described in more detail below.

As with the catheters 200 and 200', a rigid, hollow tubular needle 312 may be partially located within the lumen of the catheter body 306 and operatively fixed relative to the body, e.g., fixed to an inner surface of the guide tube 308. Stated alternatively, the guide tube may be interposed or positioned between the proximal end of the needle 312 and the inner surface of the body 306. The needle 312 may, like the needles 212 and 212', extend or protrude outwardly from the distal end of the guide tube such that a sealed distal tip 302a of the needle is located a preset distance 314 beyond the distal end of the catheter body/guide tube flange 310 as illustrated in FIGS. 4A and 4B.

Once again, the needle 312 may be nonporous and incorporate the sealed, rounded distal tip or end 302a (which forms the most-distal end of the catheter 300) as shown in FIGS. 4A-4B. As with the other needle embodiments described herein, closure of the needle tip prevents direct axial flow from the needle. However, as with the needles 212 and 212', the needle 312 may include one or more, e.g., two, side flow openings or apertures 316 formed along an outer surface of the needle and proximate to, but offset from, the sealed distal tip. Like the needles 212 and 212', the flow apertures may each have an axis that is, nonparallel to, e.g., normal to, the longitudinal axis of the catheter and/or the needle. The aperture(s) 316 are again in fluid communication with the lumen 318 of the body 306 such that therapeutic substance flowing through the lumen may pass into the needle 312 (e.g., the lumen of the needle) and out through the aperture(s) 316.

The configuration of the catheter 300 provides benefits similar to those already described above with respect to the catheters 200 and 200'. For instance, like the catheters 200 and 200', the needle 312 of the catheter 300 may have an outer surface defined by a diameter that is less than a diameter of the outer surface of the body 306. Thus, the catheter 300 provides an obstructive element, e.g., ledge 320, which may be formed by the flange portion 310 of the guide tube 308. The ledge 320 may again form a barrier that potentially reduces, via interference, backflow of therapeutic substance delivered by the catheter 300. Moreover, the relative sizes of the needle 312 and catheter body 306, as well as the side position of the flow opening(s) 316, may contribute to improved backflow characteristics.

FIGS. 5-9 illustrate the exemplary individual components of the catheter 300. FIG. 5 illustrates the flexible and shearable body 306; FIG. 6 illustrates an enlarged and partial cut-away view of the guide tube 308; FIG. 7A illustrates the needle 312; and FIGS. 7B and 7C illustrate enlarged views of a proximal end and distal end, respectively, of the needle 312.

As already described above with respect to the catheters 200 and 200', the catheter body 306 may, in one embodiment, be made of a material such as urethane. As a result, the proximal end of the catheter may be cut (e.g., shear cut) during implantation to provide the catheter with the desired length.

The guide tube 308 may be made from a variety of materials including, for example, PEEK or other thermoplastic materials. In some embodiments, the guide tube may again have a length (including the flange 310) of about 0.2 in to about 0.4 in. As illustrated in FIG. 6, the recessed land 311 may be defined by the transition existing between the larger bore diameter at the proximal end of the guide tube 308, and the smaller bore diameter extending towards the distal end.

The exemplary needle 312 may, in one embodiment, be made from 33 gage 316 hypodermic tubing having its distal tip sealed or capped to limit or prevent direct axial flow from the needle. In one embodiment, the distal end of the needle is sealed through a cold forming process or an orbital riveting operation, although other capping methods may be used. The side flow opening(s) 316 may be formed in the needle proximate to, but offset from, the distal end (e.g., by a distance 317

(FIG. 7C) of about 0.015 in) and, like the openings 216', have a diameter of about 0.004 in (generally equal to the inner diameter of the needle). The openings may be formed by a guided drilling process or, alternatively, a laser machining process. While other embodiments are possible, the illustrated needle 312 includes two side flow openings 316 that are diametrically opposed.

While effective as a delivery conduit, needles 312 constructed of stainless steel may produce undesirable artifacts when viewed under MRI. As a result, some embodiments may utilize a needle 312 constructed of platinum (Pt)-iridium (Ir) alloy. For example, a needle made from 90 Pt-10 Ir or 80 Pl-20 Ir alloy are contemplated. Needles produced from these alloys may reduce undesirable MRI artifacts without sacrificing overall catheter performance.

As perhaps best illustrated in FIGS. 4C and 7B, the needle 312, like the needle 212', may further include the flange 315 at its proximal end. The proximal end of the needle, e.g., the flange 315, may, once again, have a diameter larger than the diameter of the outer surface of the needle and may be fixed relative to the inner surface of the body 306, e.g., fixed directly to the inner surface of the guide tube 308. That is, the flange 315 may, upon insertion of the distal end of the needle 312 into the proximal end of the guide tube 308 (via the bore 319), function as a mechanical stop once the flange abuts the land 311 of the guide tube. Moreover, the flange at the proximal end of the needle 312 may permit the needle to be mechanically secured directly to an inner surface of the guide tube 308 as further described below.

As with the other embodiments illustrated herein, the distal end of the needle 312 may extend beyond the catheter body 306 and flange 310 by a preset distance 314 (e.g., about 0.4 in) when the catheter is assembled for reasons already described herein (see, e.g., implantation of the catheter 200 with the cannula 226 of FIG. 3B).

Figure 8:
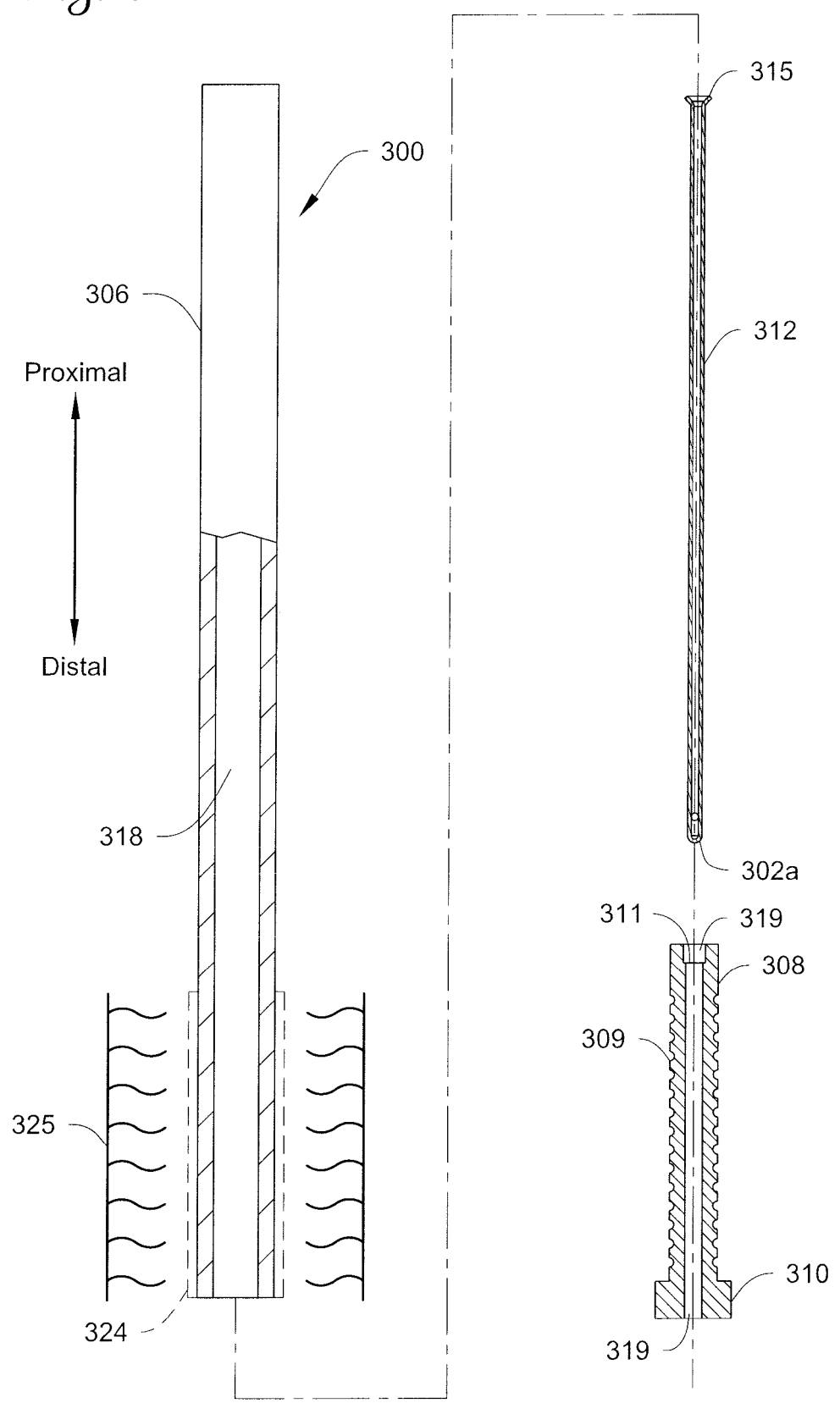
FIG. 8 is an exploded section view of the catheter of FIGS. 4A-4D illustrating a method of making the catheter in accordance with one embodiment of the invention.

An exemplary method of assembling the components of the catheter 300 will now be described primarily with reference to FIG. 8. The needle 312, e.g., the distal tip or end 302a of the needle, may be inserted into the guide tube 308 via the proximal end of the bore 319 as shown in FIG. 8. Upon complete insertion, the flange 315 of the needle may contact and rest upon the land 311 of the guide tube 308. At this point, the distal end of the needle may protrude the preset distance 314 beyond the distal end of the guide tube. Through a thermal process, the outer surface of the needle 312 (e.g., the flanged proximal end) may be fused or otherwise bonded to the inner surface of the guide tube 308. In one embodiment, this is accomplished by placing a soldering iron tip into the proximal end of the needle 312 and fusing the flange 315 of the needle to the inner surface of the guide tube. In one embodiment utilizing a Pl-Ir needle and a PEEK guide tube, the soldering iron may heat the needle locally to about 670 degrees Fahrenheit (F.) to melt it, whereupon the needle fuses to the guide tube upon cooling. Such a process not only mechanically interlocks the needle to the guide tube, but furthermore desirably seals any annular flow path between the needle and the guide tube without requiring adhesives or other intermediate materials.

Once the needle 312 is attached to the guide tube 308, the proximal end of the guide tube may be inserted into the distal end of the body 306 (into the lumen 318 of the body) until the flange portion 310 abuts the distal end of the body (see FIG. 4A). A reflow operation may then be performed to the catheter body 306 to fix or otherwise mechanically secure the guide tube 308 relative to the body (e.g., to the inner surface of the body). For example, in one embodiment, a section of heat shrink tubing 324 may be placed over the distal end of the body 306 of the catheter 300 as shown in FIG. 8. A heating element 325 (e.g., oven) may then heat the tubing 324 and the body 306. Upon reaching a threshold temperature (e.g., about 310 degrees F. for a urethane body), the body 306 may begin to reflow and bond to the guide tube 308. Reflow of the body material may result in an effective mechanical interlock or capture of the guide tube 308 with the inner surface of the body 306 as body material flows into the grooves 309 of the outer surface of the guide tube (see, e.g., FIG. 4D). The reflow operation may also effectively seal any annular flow path between the guide tube and the catheter body, generally preventing flow at the interface of these two components. At the completion of the reflowing operation, the heat element is deactivated and removed. After cooling, the heat shrink tubing 324 may be sliced and removed from the body, yielding the catheter 300 as illustrated in FIG. 4A.

Figure 9:
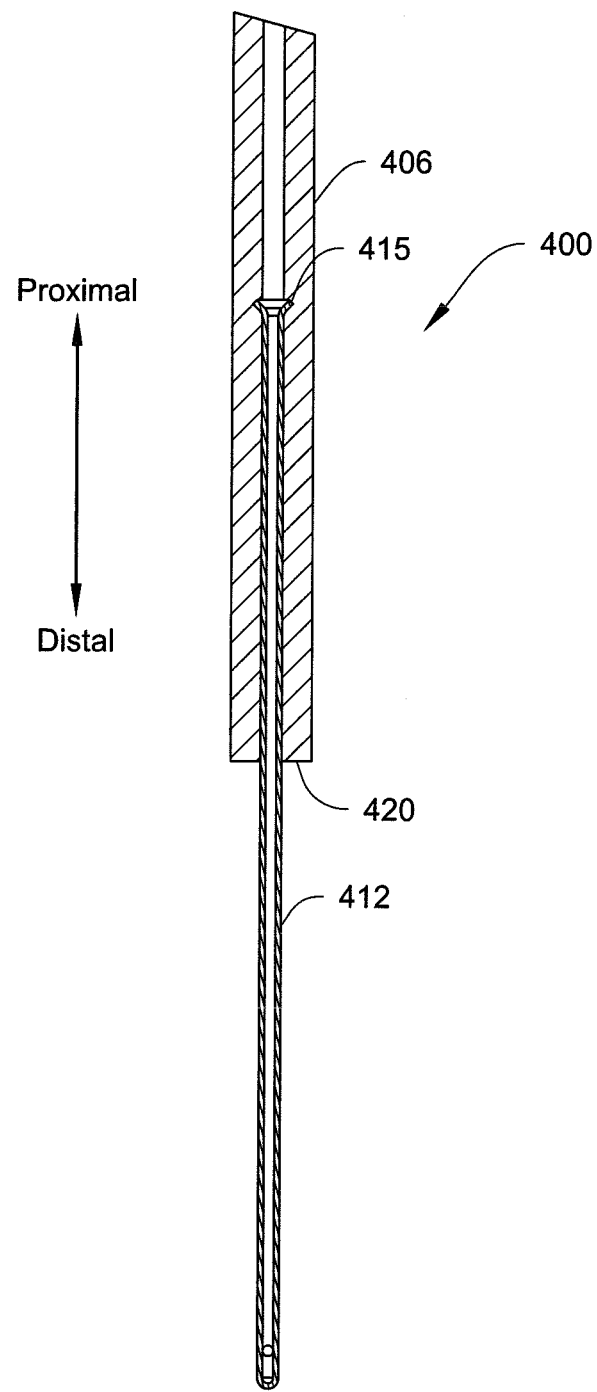
FIG. 9 is a section view of an IPA catheter in accordance with yet another embodiment of the invention.

While the use of the guide tube 308 is beneficial when a relatively large difference exists between the inner diameter of the catheter body 306 and the outer diameter of the needle 312, it may be unnecessary in other applications where this difference is slight. For example, FIG. 9 illustrates an exemplary catheter 400 similar to the catheter 300. That is, it includes a flexible and shearable catheter body 406 with a needle 412 extending from a distal end of the body. The needle 412 may be substantially identical to the needle 312 already described herein. However, the catheter body 406 may have an inner diameter that is smaller than that of the body 306 (e.g., the catheter body may have a thicker wall). In this instance, the needle may be located at the desired position within the body 306 as shown in FIG. 9. At this point, the body may be reflowed (e.g., in a manner similar to that described above with reference to the catheter 300) until it bonds with the needle 412. That is, the needle 412, e.g., the flange 415, may be fixed or otherwise secured directly to the inner surface of the body 406. While illustrated herein as using a needle having a flange 415, such a configuration is not limiting. That is, a flangeless needle (not shown) could also be used in place of the flanged needle 412 without departing from the scope of the invention. The catheter body 406 may, in this embodiment, be used to form an obstructive element, e.g., ledge 420, similar in function to the obstructive elements already described herein.

The catheters 200, 200', 300, and 400 described above provide an effective construction to reduce backflow along the catheter track. However, other configurations are also contemplated that may provide benefits similar to those already described herein. For example, FIGS. 10A and 10B illustrate enlarged views of a distal portion 502 of an IPA catheter 500 in accordance with another embodiment of the invention. Except as described herein, the catheter 500 may be used in place of the catheters 200, 200', 300, and 400 within the system 100.

FIG. 10A illustrates a perspective section view of the distal portion 502 of the catheter 500, while FIG. 10B illustrates a corresponding perspective view. The catheter 500 may include a flexible tubular body 506, an insert (e.g., guide tube 508), and a tip member or needle 512 that may be substantially similar or identical to the like components illustrated and described with respect to the catheters 200, 200', 300, or 400. For example, the guide tube 508 may include a flange 510 that abuts the distal end of the body 506 when the guide tube is fully inserted and secured to the body. Moreover, the needle 512 may extend beyond the distal end of the guide tube 508 in a manner similar to that of the catheters 200, 200', 300, and 400. In the illustrated embodiment, the needle 512 may extend a predetermined distance 514 (e.g., about 0.4 in) beyond an expanding cup or cup member 532 (described below and attached at or near the distal end of the catheter body) and include a closed distal end 502a similar to the needles described elsewhere herein. Therapeutic substance may flow through a lumen formed by the inner surface of the body 506 and a lumen of the needle 512 and out through nonaxial side flow opening(s) 516.

The catheter 500, unlike the catheter described above, however, may also include the cup 532. In one embodiment, the cup 532 may be made from a relatively flexible material such as silicone. The cup may thus collapse for fitting within a delivery/removal cannula 526 (see FIG. 10B), but may expand as illustrated in FIGS. 10A and 10B when the cannula is withdrawn. The cup 532 may be secured or otherwise bonded to the flange 510 of the guide tube 508 and/or the needle 512, or alternatively, to an outer surface of the catheter body 506. In one embodiment, the cup 532 may have a maximum or unconstrained O.D. of about 0.08 in (when used with a catheter otherwise sized as described above with reference to the catheter 200).

Like the ledge 220 provided by the catheter 200, the cup 532 of the catheter 500 also provides an obstructive element, e.g., an undercut ledge 520. The undercut ledge may, in some applications, further assist with backflow prevention as already described above. Moreover, an outer surface of the cup 532 may, upon withdrawal of the cannula 526 and expansion of the cup, generate a compressive seal with the immediately surrounding tissue. This seal may further assist with reducing catheter backflow.

The catheter 500 may be removed by application of a traction force. Upon withdrawal, the shape of the cup 532 may be such that it collapses to a size about equal to the outer diameter of the catheter body 506 and thus can withdraw through the catheter passageway without difficulty. Alternatively, the cannula 526 may be placed over the catheter body 506 and cup 532. Once again, the shape of the cup 532 may permit the cannula to slide over and squeeze the cup until the body and cup are contained within the cannula.

Figure 10C:
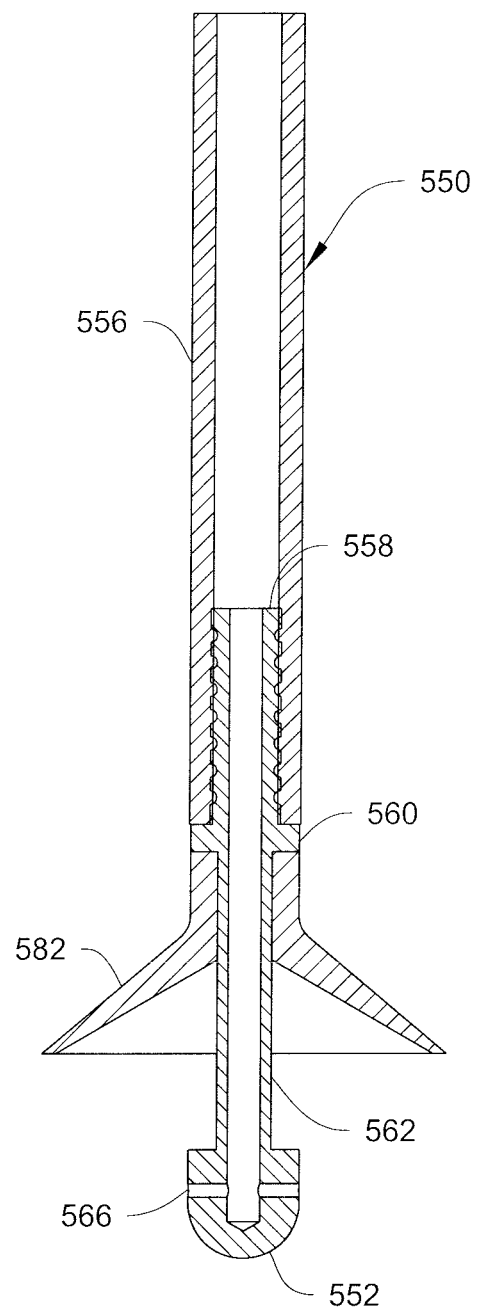
FIG. 10C illustrates a section view of an IPA catheter assembly in accordance with still another embodiment of the invention.

FIG. 10C illustrates a section view of an IPA catheter 550 similar in many respects to the IPA catheter 500 of FIGS. 10A-10B and could be used in place of the latter. The catheter 550 may once again include a flexible tubular body 556. A distal portion 552 of the catheter 550 may be formed by an insert or guide tube 558 located within the distal end of the body 556. The insert 558, like the guide tube 508, may include a flange 560 that abuts the distal end of the body 556 as shown. While the insert 558 may be similar in many respects to the guide tube 608, it may further include an integral needle 562 defining a nonaxial side flow opening(s) 566. As FIG. 10C illustrates, the catheter 550, like the catheter 500 described above, may also include the cup 582. The cup 582 may be more conical in shape than the cup 532. However, its functionality is generally the same as that described above with respect to the catheter 500. Therefore, further description of the catheter 550 is not provided herein.

FIGS. 11A and 11B illustrate enlarged views of a distal portion 602 of an IPA catheter 600 in accordance with yet another embodiment of the invention. Once again, except as described herein, the catheter 600 could be used in place of, the catheters 200, 200', 300, 400, 500, and 550 in the system 100.

FIG. 11A illustrates an inflatable balloon (described in more detail below) associated with the catheter in a deflated configuration, while FIG. 11B illustrates the balloon inflated. The catheter 600 may, like the others described herein, includes a flexible tubular body 606 forming a lumen 618 through which therapeutic substance may be delivered. Moreover, the catheter 600 includes an insert. However, rather than a guide tube arrangement and needle like that described, for example, with respect to the catheters 200 and 300, the insert of the catheter 600, like the insert 558, may form an axially closed tip or tip member 609 having a distal end 602a. The tip 609 may include a body portion configured to secure to the catheter, e.g., within the lumen 618 as shown. The tip 609 may be secured, e.g., bonded, to the catheter body 606 via any acceptable technique.

The closed tip 609 may form the distal end 602a of the catheter and axially seal the distal end of the catheter body 606 as shown in FIG. 11A. One or more nonaxial, e.g., side flow, openings 616 may be formed in the closed tip 609 to permit side exiting flow of therapeutic agent from the catheter in a manner similar to the catheters 200, 200', 300, 400, 500, and 550 described above. In one embodiment, the tip is a made from tantalum and has an O.D. of about 0.041 in and an I.D. of about 0.020 in, while the side flow opening(s) 416 are laser holes having a diameter of about 0.0002 in. By providing holes of this size, a 1-2 psi backpressure may be created in the catheter during CED infusion. Once again, this embodiment is exemplary only and catheters having components sized and configured differently are certainly possible without departing from the scope of the invention.

The catheter 600 may further include an inflatable balloon 632 attached at or near the distal end of the catheter body. In one embodiment, the balloon 632 may be made from a relatively flexible and resilient material such as urethane. By utilizing a resilient material, the balloon may constrict and lie generally against the body 606 of the catheter as shown in FIG. 11A when it is deflated. However, when inflated, the balloon may expand to form a cup as shown in FIG. 11B. The balloon 632 may be secured, e.g., thermally bonded, to the body 606 of the catheter as represented in the figures. In one embodiment, the balloon 632 may have a maximum outer diameter of about 0.08 in (when used with a catheter body otherwise sized and configured as described above with reference to the catheter 200).

When the balloon 632 is inflated, it may form an obstructive element, e.g., undercut ledge 620. As with the ledge 520, the ledge 620 may, in some applications, assist with reduction of backflow. Moreover, like the cup 532, the cup formed by the balloon 632 may generate a compressive seal with the immediately surrounding tissue. This seal may further assist in reducing catheter backflow. As with the prior embodiments, the ledge 620 may be offset from the end 602a by a predetermined distance 614 (e.g., about 0.4 in).

Once implanted (e.g., via a cannula (not shown) and after the cannula is withdrawn), the catheter 600 may be reconfigured from the balloon-deflated configuration of FIG. 11A to the balloon-inflated configuration of FIG. 11B. In one embodiment, inflation is initiated by the infusion process itself. For example, the catheter body 606 may define one or more openings 611 in fluid communication with the sealed compartment formed by the balloon 632. Due to the backpressure resulting from the restrictive orifice 616, the balloon may inflate to its cup-shaped configuration of FIG. 11B once infusion begins. The balloon 632 may, correspondingly, deflate when infusion pressure is removed. The catheter 600 may be removed, in one embodiment, by placing a removal cannula (not shown) over the body and the deflated balloon and withdrawing the catheter from the proximal end. Alternatively, the collapsed balloon may simply be withdrawn with the body by application of a traction force (e.g., without the need for a removal cannula).

Figure 12:
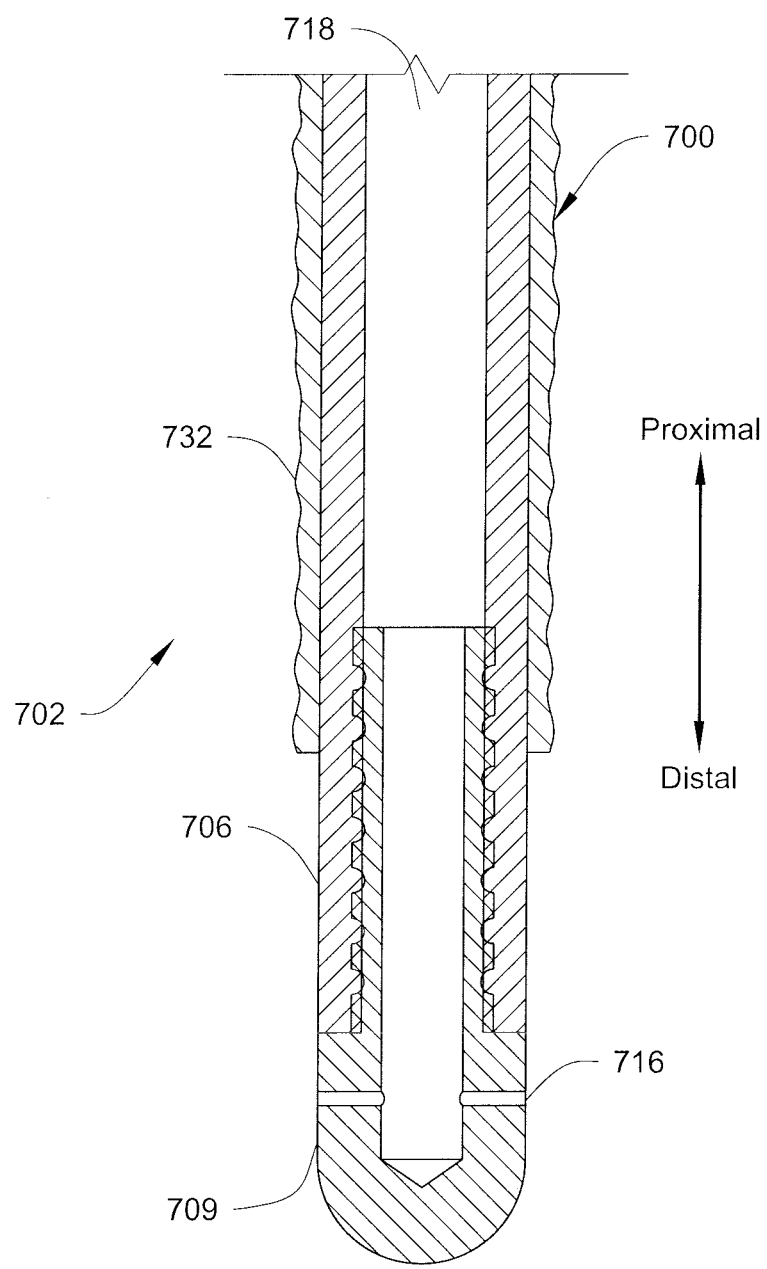
FIG. 12 illustrates an enlarged view of a distal portion of an IPA catheter in accordance with yet another embodiment of the invention.
Figure 13A:
FIGS. 13A-13D are MRI images of contrast dispersion occurring with conventional uniform diameter, axial flow catheters when implanted in four different in vivo specimens.
Figure 13B:
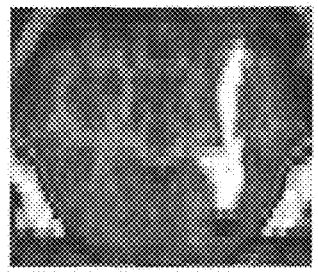
Figure 13C:
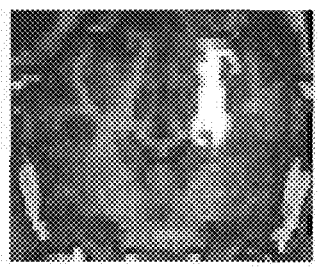
Figure 13D:
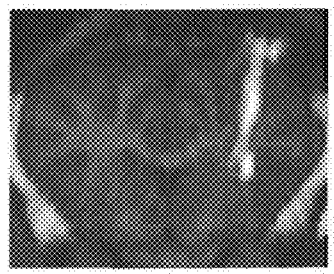

FIG. 12 illustrates an enlarged view of a distal portion, e.g., a distal portion 702 of an IPA catheter 700 in accordance with still yet another embodiment of the invention. The catheter 700 may, except as described below, be similar in many respects to the catheters already described herein. For example, the catheter 700 may include a body 706 and an insert, e.g., closed tip 709, similar in many respects to the body 606 and tip 609 discussed above. The tip 709 may include a body portion that bonds or is otherwise secured to a lumen 718 of the body 706. The closed tip may further include one or more nonaxial, e.g., side flow, openings 716 to permit the delivery of therapeutic substance to surrounding tissue.

The catheter 700 may further include an obstructive element. In the illustrated embodiment, the obstructive element could be formed by a hydrogel coating 732 applied to a portion of the catheter body. The hydrogel coating 732 may form an expanding gel upon contact with water, bodily fluids, etc. This gel may fill the voids between the catheter body and the surrounding tissue and thus form an obstructive barrier to backflow similar to the barrier provided by the ledge 620 described above. While illustrated without a structural ledge, the hydrogel coating could be combined with any of the other anti-backflow embodiments described herein, e.g., the ledges 220, 320, and 420 of the catheters 200, 300, and 400, respectively.

Although not shown herein, various techniques (e.g., use of a stylet) may be utilized with any of the embodiments described herein to assist with stiffening of the catheter during surgical implantation. Furthermore, while specific embodiments are described and illustrated herein, various characteristics of these illustrative catheter assemblies (such as the diameter of the outer surface of the needle/insert, the diameter of the outer surface of the body, and the preset distance) may be varied. These parameters may be selected to minimize or reduce backflow along the catheter during therapy delivery such as during CED of therapeutic agent to a target tissue region of a mammalian brain.

As a result, embodiments of the present invention may also be directed to methods for delivery (CED delivery) of a therapeutic substance to a target tissue region (e.g., to a patient's brain) using a catheter assembly in accordance with embodiments of the present invention. For example, a catheter assembly as shown and described herein (e.g., catheter assembly 300) may be provided. The catheter assembly may be positioned such that a distal end of the tubular needle is implanted within the target tissue region. A therapeutic substance may be infused into the target tissue region through the lumen (e.g., 318) via CED from the side flow apertures (e.g., 316) of the catheter assembly at a substantially constant flow rate and for a predetermined period of time. Where the catheter assembly, e.g., distal end of the catheter assembly, is implanted in or near a target tissue region, CED of the therapeutic agent may thus be administered using an assembly configured to assist with the reduction of backflow of the therapeutic agent. Accordingly, the therapeutic substance may disperse into the target tissue region primarily in a spherical pattern emanating outwardly from or near the side flow apertures without significant backflow occurring along the catheter track.

EXAMPLE

A baseline analysis was conducted to determine backflow characteristics of a uniform diameter, axial flow flexible catheter. In particular, a catheter having uniform inner and outer diameters was selected for implantation in vivo into sheep brain specimens. These catheters were made from 80 Shore A durometer urethane and each had an inner diameter of about 0.024 in and an outer diameter of about 0.041 in. In these tests, the catheters were implanted into the tissue of four specimens (two into the putamen and two into the white matter) and gadolinium-bound albumin contrast agent infusate was acutely administered via the catheter.

For the first test, the infusate was administered at 0.5 microliters/minute. A second test administered the infusate at a flow rate of 2.5 microliters/minute, while a third test was run at 5 microliters/minute. Each test was administered at its particular constant flow rate for a period of seven days using a SyncroMed® II programmable pump. The tissue samples were then examined under MRI. One of the four samples showed backflow at a flow rate of 0.5 microliters/minute. All four specimens showed backflow at 2.5 microliters/minute, and three showed backflow at 5 microliters/minute (no data was collected on the fourth sample at this highest flow rate).

Backflow was recognized by clearly defined flow of the contrast agent along the catheter delivery track, indicating a potential break in the fluidic seal between the catheter and the surrounding tissue. In fact, in some instances the infusate was detected even at the catheter insertion point into the specimen, indicating catastrophic backflow (e.g., along the entire catheter length). FIGS. 13A-13B and 13C-13D show the two putamen and two white matter infusions, respectively, for the 2.5 microliters/minute flow rate tests. The elongate white sections in these views illustrate back flow of the contrast agent along the catheter track.

These uniform diameter catheters were then implanted in vitro into four cadaveric sheep brain tissue samples to a depth of about 0.59 in. Evans blue dye was infused at a flow rate of about 0.5 microliters/minute and increased in steps every ten minutes until catastrophic backflow was detected (e.g., dye was observed emerging from the entry point of the catheter into the brain tissue). The infusion device used was a model PHD 2000 syringe pump from Harvard Apparatus of Holliston, Mass., USA. Three of the four samples indicated catastrophic backflow at the initial flow rate of 0.5 microliters/minute, while the fourth sample indicated catastrophic backflow at about 5 microliters/minute.

Thereafter, catheter assemblies in accordance with embodiments of the present invention (catheter assemblies configured generally as shown and described with respect to the assembly 300 of FIGS. 4A-4D) were tested in vitro in four cadaveric sheep brain tissue samples in a manner similar to the in vitro uniform diameter catheter tests. In these tests using catheter assemblies constructed in accordance with principles of the present invention, all four assemblies showed no catastrophic backflow at rates up to about 30 microliters/minute.

Catheter assemblies constructed in accordance with embodiments of the present invention were then tested in vivo in non-human primate brains. In these tests, a catheter assembly was used that was, once again, configured generally as shown and described with respect to the assembly 300 of FIGS. 4A-4D. The catheters were implanted through the cranium and their proximal ends anchored relative thereto with silicone elbows. These assemblies used a catheter body 306 made from 80 Shore A durometer urethane having an inner diameter of about 0.024 in and an outer diameter of about 0.041 in. They further incorporated a guide tube 308 made of PEEK with a length (including the flange 310) of about 0.4 in. The needle 312 was a 33 gage needle made from 80 Pt-20 Ir alloy with a distal tip 302a sealed via an orbital riveting operation. It had two side flow apertures 316 of about 0.004 in diameter and located about 0.015 in from the sealed distal tip 302a. The preset distance 314 was about 0.2 in.

In a one-day acute infusion test, three subjects were infused with 1.0 microliter/minute using gadolinium (available under the trade name Omniscan from GE Healthcare of Chalfont St.

Figure 14:
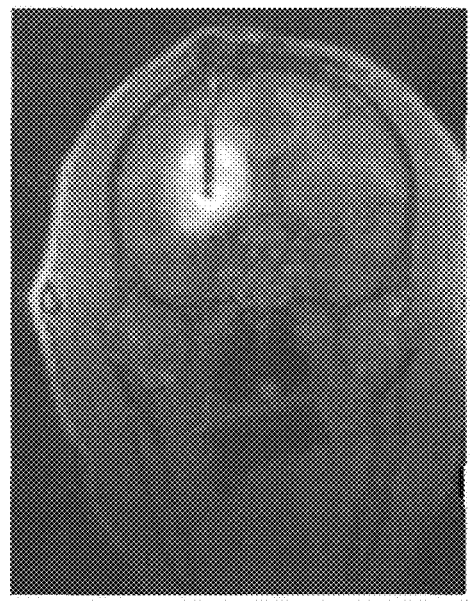
FIG. 14 illustrates an MRI image of contrast dispersion in an in vivo subject when using a catheter assembly constructed in accordance with one embodiment of the present invention.

Giles, United Kingdom) contrast agent for a period of about six hours (for a total infusion of 360 microliters) using the model PHD 2000 syringe pump. Thereafter, the flow rate was increased to 30 microliters/minute for a period of three minutes (for a total of 90 microliters). Using magnetic resonance imaging, no discernable backflow was observed at either flow rate in the test subjects. FIG. 14 illustrates an exemplary MRI scan from one test specimen. As shown in this view, two white circular areas are seen emanating outwardly from near the distal end of the catheter and illustrate the infusate distributions. The larger area illustrates the infusate distribution from the six hour infusion, while the smaller, more concentrated area illustrates the infusate distribution resulting from the three minute infusion. As this figure illustrates, there appears to be little or no indication of contrast agent flowing along the catheter track beyond the visible distribution areas, indicating that little if any significant backflow occurred (note: one test subject indicated possible catheter movement during testing while another catheter developed a leak at its proximal end coupling).

In a chronic seven day infusion test, catheter assemblies were implanted within the brains of six non-human primates and gadopentetate dimeglumine contrast agent (available under the trade name Magnevist from Bayer HealthCare Pharmaceuticals of Wayne, N.J., USA) was infused (using a SyncroMed® II programmable pump) at various flow rates from 0.1 to 1.0 microliters/minute for a period of seven days (for a total of 10 milliliters infused). Once again, no significant backflow was observed at these flow rates, although one subject did show signs of catheter movement as a result of test anchoring configurations that were potentially ill-suited to such chronic treatment. In a corresponding toxicity study, 26 non-human subjects were infused at 0.3 microliters/minute with various concentrations of siRNA for up to 28 days (for a total of 12 milliliters infused). During this test, no significant backflow was observed in the subjects (4 subjects did not indicate any flow at all through the catheter, indicating possible plugging, e.g., tissue ingrowth, of the catheter prior to or during testing).

Catheters constructed in accordance with embodiments of the present invention may thus reduce catheter backflow when compared to conventional catheter constructions. Various design parameters are believed to contribute to this reduced backflow. For instance, it is believed that the relatively small diameter (e.g., 33 gage) of the needle may be advantageous in reducing backflow when compared to larger catheters of uniform diameter. Moreover, embodiments of the present invention may potentially benefit from the obstruction of flow from the needle tip as provided by obstructive elements such as those shown and described herein (e.g., the step formed by the smaller diameter needle joining to the relatively larger catheter body). Still further, catheters in accordance with embodiments of the present invention may, instead of providing axial flow, provide one or more side flow opening(s) proximate to, but offset from, the distal tip. These side flow openings may also contribute to a reduction in backflow.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Rather, the invention is limited only by the claims provided below, and equivalents thereof.

What is claimed is:

1. A catheter assembly comprising:
   a flexible tubular catheter body having proximal and distal ends, the body comprising an inner surface defining a lumen extending between the proximal and distal ends;
   a guide tube fixed to the inner surface of the body near the distal end of the body;
   a tubular needle fixed to an inner surface of the guide tube so as to restrict any relative axial movement therebetween, wherein the needle comprises: a proximal end forming a flange; and a protruding portion that extends distally beyond a terminal distal end face of the guide tube, the protruding portion of the needle comprising:
      an outer surface defined by a diameter that is less than a diameter of an outer surface of the guide tube; and
      a sealed distal tip located a preset distance beyond the distal end face of the guide tube, the needle defining at least two side flow apertures formed along the outer surface of the needle proximate to, but offset from, the sealed distal tip, the side flow apertures in fluid communication with the lumen of the body.

2. The assembly of claim 1, wherein the flange of the needle is fixed directly to the inner surface of the guide tube.

3. The assembly of claim 2, wherein the flange of the needle is fused to the inner surface of the guide tube.

4. The assembly of claim 1, wherein the inner surface of the guide tube defines a stepped bore forming a land to contact the flange of the needle.

5. The assembly of claim 4, wherein the guide tube further comprises a sleeve portion having an outer surface, the outer surface defining one or more circumferential grooves into which inwardly protruding portions of the body extend.

6. A catheter assembly comprising:
   an elastomeric and shearable tubular catheter body comprising proximal and distal ends, the body comprising an inner surface and an outer surface, the inner surface defining a lumen extending between the proximal and distal ends;
   a guide tube fixed to the inner surface of the body, wherein the guide tube comprises a proximal end located intermediate the proximal and distal ends of the body, and a distal end comprising a flange that abuts a terminal distal end face of the body and defines an obstructive element normal to a longitudinal axis of the guide tube; and
   a tubular needle comprising an outer surface defined by a diameter that is less than a diameter of an outer surface of the guide tube, wherein the needle comprises a proximal end located intermediate the proximal and distal ends of the body, the needle fixed to the guide tube and protruding outwardly such that a sealed distal tip of the needle is located a preset distance beyond the flange, the needle defining one or more flow apertures proximate to, but offset from, the sealed distal tip, each flow aperture having an axis that is normal to a longitudinal axis of the needle and is in fluid communication with the lumen of the body, wherein the diameter of the outer surface of the needle, a diameter of the outer surface of the body, and the preset distance are selected to reduce backflow along the needle and body during convection enhanced delivery of a therapeutic agent to a target tissue region of a mammalian brain.

7. The assembly of claim 6, wherein the diameter of the outer surface of the needle is about 0.006 inches to about 0.010 inches.

8. The assembly of claim 6, wherein the preset distance is about 0.2 inches to about 0.5 inches.

9. The assembly of claim 6, wherein a ratio of the diameter of the outer surface of the body to the diameter of the outer surface of the needle is about 4:1 to about 6:1.

10. A method for delivery of a therapeutic substance to a target tissue region in a patient's brain, the method comprising:
    implanting into the target tissue region a distal end of a tubular needle of a catheter assembly, wherein the catheter assembly comprises:
        a flexible tubular catheter body having proximal and distal ends, the body comprising an inner surface defining a lumen extending between the proximal and distal ends;
        a guide tube fixed to the inner surface of the body near the distal end of the body; and
        the tubular needle, wherein the tubular needle is fixed to an inner surface of the guide tube so as to restrict any relative axial movement therebetween, wherein the needle comprises a protruding portion that extends distally beyond a terminal distal end face of the guide tube, the protruding portion of the tubular needle comprising:
            an outer surface defined by a diameter that is less than a diameter of an outer surface of the guide tube; and
            a sealed distal tip located a preset distance beyond the distal end face of the guide tube, wherein the needle defines at least two side flow apertures formed along the outer surface of the needle proximate to, but offset from, the sealed distal tip, the side flow apertures in fluid communication with the lumen of the body; and
    infusing the therapeutic substance into the target tissue region through the lumen at a constant flow rate via convection enhanced delivery from the side flow apertures.

11. The method of claim 10, further comprising dispersing the therapeutic substance to the target tissue region in a spherical pattern emanating outwardly from or near the side flow apertures, wherein no significant backflow of the therapeutic substance occurs.

12. A catheter assembly comprising:
    a flexible tubular catheter body having proximal and distal ends, the body comprising an inner surface defining a lumen extending between the proximal and distal ends;
    a guide tube fixed to the inner surface of the body near the distal end of the body;
    wherein the guide tube comprises a proximal end located intermediate the proximal and distal ends of the body, and a distal end comprising a flange that abuts a terminal distal end face of the body and defines an obstructive element normal to a longitudinal axis of the guide tube; and
    a tubular needle, wherein the tubular needle is fixed to an inner surface of the guide tube so as to restrict any relative axial movement therebetween, wherein the needle comprises a protruding portion that extends distally beyond a terminal distal end face of the guide tube, the protruding portion of the tubular needle comprising:
        an outer surface defined by a diameter that is less than a diameter of an outer surface of the guide tube; and
        a sealed distal tip located a preset distance beyond the distal end of the guide tube, wherein the needle defines at least two side flow apertures proximate to, but offset from, the sealed distal tip, the side flow apertures in fluid communication with the lumen of the body.

* * * * *